United States Patent
Dykstra et al.

(10) Patent No.: US 7,109,153 B2
(45) Date of Patent: Sep. 19, 2006

(54) PHOTO-LABILE PRO-FRAGRANCE CONJUGATES

(75) Inventors: Robert Richard Dykstra, Cleves, OH (US); Gregory Scot Miracle, Hamilton, OH (US); Lon Montgomery Gray, Florence, KY (US)

(73) Assignee: Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/148,688

(22) Filed: Jun. 9, 2005

(65) Prior Publication Data

US 2005/0245408 A1 Nov. 3, 2005

Related U.S. Application Data

(62) Division of application No. 10/693,733, filed on Oct. 24, 2003, now Pat. No. 6,987,084, which is a division of application No. 10/001,029, filed on Nov. 2, 2001, now abandoned.

(60) Provisional application No. 60/246,811, filed on Nov. 8, 2000.

(51) Int. Cl.
C11D 3/50 (2006.01)
(52) U.S. Cl. .................. 510/103; 512/10; 548/215
(58) Field of Classification Search .............. 548/215; 510/103; 512/10
See application file for complete search history.

(56) References Cited

U.S. PATENT DOCUMENTS

| | | | |
|---|---|---|---|
| 3,547,903 A | 12/1970 | Cron et al. | |
| 6,096,918 A | 8/2000 | Anderson et al. | |
| 6,479,682 B1 | 11/2002 | Anderson et al. | |
| 6,544,945 B1* | 4/2003 | Miracle et al. | 512/27 |
| 6,551,987 B1* | 4/2003 | Miracle et al. | 512/2 |
| 6,861,402 B1* | 3/2005 | Miracle et al. | 512/2 |
| 6,956,013 B1* | 10/2005 | Dykstra et al. | 510/107 |
| 6,987,084 B1 | 1/2006 | Dykstra | |

FOREIGN PATENT DOCUMENTS

| | | |
|---|---|---|
| DE | 1 058 067 | 3/1956 |
| EP | 0 526 302 A1 | 2/1993 |
| EP | 936211 A2 * | 1/1999 |
| EP | 0 936 211 A2 | 8/1999 |
| EP | 0 952142 A1 | 10/1999 |
| EP | 983990 A2 * | 3/2000 |
| WO | WO 97/34986 | 9/1997 |
| WO | WO 00/63339 * | 10/2000 |
| WO | WO 00/63339 A1 | 10/2000 |
| WO | WO 01/91712 A2 | 12/2001 |
| WO | WO 02/38120 * | 5/2002 |

OTHER PUBLICATIONS

H Jaggy, Planta Med., A Spermidine Derivative from Crataegus Blossoms, No. 33, 1978, p. 285, XP-002192935.
A Zheng et al., Tetrahedron, vol. 55, pp. 4237-4254, Jul. 1999.
International Search Report.

* cited by examiner

*Primary Examiner*—John R. Hardee
(74) *Attorney, Agent, or Firm*—James F. McBride; Kim W. Zerby; Steve W. Miller

(57) ABSTRACT

The present invention relates to photo-labile pro-fragrance conjugates comprising:
  a) a photo-labile unit which upon exposure to electromagnetic radiation is capable of releasing a pro-fragrance unit; and
  b) a pro-fragrance unit, which when so released is either
     i) a pro-fragrance compound capable of releasing a fragrance raw material; or
     ii) a fragrance raw material.

The present invention relates to systems for delivering fragrances to a situs, and to laundry detergent compositions, fine fragrances, personal care and hair care compositions comprising said systems.

9 Claims, No Drawings

PHOTO-LABILE PRO-FRAGRANCE CONJUGATES

CROSS REFERENCE TO RELATED APPLICATIONS

This application is a divisional of and claims priority under 35 U.S.C. § 120 to U.S. application Ser. No. 10/693,733 filed Oct. 24, 2003, (now U.S. Pat. No. 6,987,084), which in turn is a divisional of and claims priority under 35 U.S.C. § 120 to U.S. application Ser. No. 10/001,029, filed Nov. 2, 2001, (now abandoned) which in turn claims priority under 35 U.S.C. § 119(e) to U.S. Provisional Application Ser. No. 60/246,811, filed Nov. 8, 2000 (now abandoned).

FIELD OF THE INVENTION

The present invention relates to photo-labile pro-fragrance conjugates, which are capable of releasing a fragrance raw material in a sequence of chemical reaction steps that include a photo-activated release of a nitrogen-containing pro-fragrance compound. The conjugates are useful in formulating fragrance delivery systems. The conjugates of the present invention are capable of delivering any type of fragrance raw material.

BACKGROUND OF THE INVENTION

Pro-fragrances and pro-accords have been used to enhance the delivery of fragrance raw materials and to sustain their duration. Typically pro-fragrances and pro-accords deliver alcohol, ketone, aldehyde, and ester fragrance raw materials via substrates which are hydrolyzed by one or more mechanisms, inter alia, the acidic pH of skin, nascent moisture.

Fragrances or odors not only provide a pleasant aesthetic benefit, but also serve as a signal. For example, foods, which have soured or are no longer edible, may develop smells, which are repulsive and send a signal that they are no longer palatable. Therefore, the delivery of an aroma sensory signal is also a benefit, which a pro-fragrance can provide.

However, pro-fragrances and pro-accords typically rely on the break down of a chemical species not based on accidental circumstance but on deliberate execution. There are currently no fragrance or odor releasing compounds which involve release of fragrances by way of a controlled chemical cascade initiated by exposure to electromagnetic radiation, inter alia, UV light. The present invention provides a means for delivering a fragrance or an accord wherein the delivery of said fragrance or said accord is instigated by exposure to light.

SUMMARY OF THE INVENTION

The present invention meets the aforementioned need in that it has been surprisingly discovered that fragrance raw materials can be delivered by photo-labile pro-fragrance conjugates. The photo-labile pro-fragrance conjugates of the present invention are activated by the exposure of the conjugates to electromagnetic radiation, which is the initial step in a chemical cascade resulting in the ultimate release of a fragrance raw material. One of the steps in the cascade involves photochemically initiated fragmentation of a chemical bond between a photo-labile unit and a nitrogen atom contained within a pro-fragrance unit.

The conjugates of the present invention comprise:
a) a photo-labile unit which upon exposure to electromagnetic radiation is capable of releasing a pro-fragrance unit; and
b) a pro-fragrance unit, which when so released is either
   i) a pro-fragrance compound capable of releasing a fragrance raw material; or
   ii) a fragrance raw material.

The present invention also relates to a photo-labile fragrance conjugate delivery system comprising:
A) from about 0.001% by weight, of a photo-labile pro-fragrance conjugate, said conjugate comprising:
   a) a photo-labile unit which upon exposure to electromagnetic radiation is capable of releasing a pro-fragrance unit;
   b) a pro-fragrance unit, which when so released is either
      i) a pro-fragrance compound capable of releasing a fragrance raw material; or
      ii) a fragrance raw material; and
B) the balance carriers and adjunct ingredients.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference.

DETAILED DESCRIPTION OF THE INVENTION

The present invention relates to photo-labile pro-fragrance conjugates, which are stable until activated by exposure to electromagnetic radiation. The conjugates of the present invention are capable of releasing any type of perfume raw material, inter alia, alcohols, ketones, aldehydes, via a single- or multi-step process that is initiated by the photo-induced fragmentation of a chemical bond between the photo-labile unit and a nitrogen atom in the pro-fragrance unit.

The conjugates of the present invention can be depicted as compounds having a photo-labile unit and a pro-fragrance unit which are connected to one another directly or optionally by way of a linking unit. The conjugates can be represented by the formula:

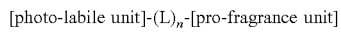
[photo-labile unit]-(L)$_n$-[pro-fragrance unit]

wherein the linking unit, L, is present when the index n is equal to 1 and absent when n is equal to 0.

For the purposes of the present invention the term "photo-labile unit" is defined herein as "a unit which upon exposure to electromagnetic radiation becomes the photo-fragment compound by fragmenting from the parent photo-labile pro-fragrance conjugate." In some embodiments of the present invention it may be advantageous that the photo-fragment compound does not interfere with the aesthetic quality or character of the released fragrance or pro-fragrance compound. In the presence of light, the photo-labile unit serves to trigger the chemical reaction or reaction cascade that ends with the ultimate release of one or more fragrance raw materials.

For the purposes of the present invention the term "pro-fragrance unit" is defined herein as "that portion of the photo-labile pro-fragrance conjugate, which gives rise to the fragrance compound or pro-fragrance compound as a result of exposure of the photo-labile pro-fragrance conjugate to electromagnetic radiation or "light."

For the purpose of the present invention the term "pro-fragrance compound" is defined herein as "a chemical species, which by undergoing one or more chemical transformations results in the release of one or more fragrance compounds." Fragrance compounds and fragrance raw materials are terms which refer to the final "perfume" ingredients which are delivered and are used interchangeably herein. What is meant herein by the term "chemical transformation" includes conversion to a species of different molecular formula by any means, inter alia, hydrolysis, photolysis, thermolysis, autoxidation, addition, elimination and substitution reactions, as well as conversion to a species with the same molecular formula, but having an altered chemical orientation, i.e., isomerized.

The chemical cascade, which begins the release of a fragrance raw material, may be controlled by requiring a certain wavelength of electromagnetic radiation to be present to initiate the release sequence. For example, "outside light", which typically comprises the full range of UV light, may be required to initiate the release of the fragrance precursor. In some cases, high temperatures may also initiate the chemical cascade.

Photo-labile Pro-fragrance Conjugates

The present invention relates to conjugates, which upon exposure to visible light or other forms of electromagnetic radiation, inter alia, UV light, releases a fragrance raw material after a series of chemical transformations, wherein said series involves at least two discrete steps. The photo-labile pro-fragrance conjugates of the present invention comprise:
 a) a photo-labile unit, which upon exposure to electromagnetic radiation is capable of releasing a pro-fragrance unit; and
 b) a pro-fragrance unit, which when so released is either
  i) a pro-fragrance compound capable of releasing a fragrance raw material; or
  ii) a fragrance raw material.

The conjugates of the present invention comprise a chemical species having a photo-activated unit which is bonded to the nitrogen atom of a pro-fragrance compound, a fragrance raw material, or a linking unit which is subsequently bonded to the nitrogen atom of a pro-fragrance compound, or a fragrance raw material, wherein said chemical bond is capable of being broken when said conjugate is exposed to electromagnetic radiation.

For the purposes of the present invention the term "hydrocarbyl" is defined herein as "any unit which comprises carbon and hydrogen atoms, whether linear, branched, cyclic, and regardless of how many of the hydrogen atoms are substituted for with a suitable "substituted" unit as defined herein below." Non-limiting examples of "hydrocarbyl" units include methyl, benzyl, 6-hydroxyoctanyl, m-chlorophenyl, 2-(N-methylamino)propyl, and the like.

The terms "unit which can substitute for hydrogen" and "substituted" are used throughout the specification and for the purposes of the present invention these terms are defined as "chemical moieties which can replace a hydrogen atom on a hydrocarbon chain, an aryl ring, and the like, or replacement of a hydrogen atom, two hydrogen atoms, or three hydrogen atoms from a carbon atom to form a moiety, or the replacement of hydrogen atoms from adjacent carbon atoms to form a moiety." For example, a substituted unit that requires a single hydrogen atom replacement includes halogen, hydroxyl, and the like. A two-hydrogen atom replacement includes carbonyl, oximino, and the like. Three hydrogen replacements includes cyano, and the like. The term substituted is used throughout the present specification to indicate that a moiety, inter alia, aromatic ring, alkyl chain, can have one or more of the hydrogen atoms replaced by a substituent. For example, 4-hydroxyphenyl is a "substituted aromatic carbocyclic ring", and 3-guanidinopropyl is a "substituted $C_3$ alkyl unit."

The following are non-limiting examples of moieties, which can replace hydrogen atoms on carbon to form a "substituted hydrocarbyl" unit:
 i) —NHCOR$^{30}$;
 ii) —COR$^{30}$;
 iii) —COOR$^{30}$;
 iv) —COCH=CH$_2$;
 v) —C(=NH)NH$_2$;
 vi) —N(R$^{30}$)$_2$;
 vii) —NHC$_6$H$_5$;
 viii) =CHC$_6$H$_5$;
 ix) —CON(R$^{30}$)$_2$;
 x) —CONHNH$_2$;
 xi) —NHCN;
 xii) —OCN;
 xiii) —CN;
 xiv) F, Cl, Br, I, and mixtures thereof;
 xv) =O;
 xvi) —OR$^{30}$;
 xvii) —NHCHO;
 xviii) —OH;
 xix) —NHN(R$^{30}$)$_2$;
 xx) =NR$^{30}$;
 xxi) =NOR$^{30}$;
 xxii) —NHOR$^{30}$;
 xxiii) —CNO;
 xxiv) —NCS;
 xxv) =C(R$^{30}$)$_2$;
 xxvi) —SO$_3$M;
 xxvii) —OSO$_3$M;
 xxviii) —SCN;
 xxix) —P(O)H$_2$;
 xxx) —PO$_2$;
 xxxi) —P(O)(OH)$_2$;
 xxxii) —SO$_2$NH$_2$;
 xxxiii) —SO$_2$R$^{30}$;
 xxxiv) —NO$_2$;
 xxxv) —CF$_3$, —CCl$_3$, —CBr$_3$;
 xxxvi) and mixtures thereof;

wherein R$^{30}$ is hydrogen, $C_1$–$C_{20}$ linear or branched alkyl, $C_6$–$C_{20}$ aryl, $C_7$–$C_{20}$ alkylenearyl, and mixtures thereof; M is hydrogen, or a salt forming cation. Suitable salt forming cations include, sodium, lithium, potassium, calcium, magnesium, ammonium, and the like. Non-limiting examples of an alkylenearyl unit include benzyl, 2-phenylethyl, 3-phenylpropyl, 2-phenylpropyl.

Photo-labile Units

The photo-labile units of the present invention may be any moiety, which is capable of instigating the release of a fragrance raw material by breaking the chemical bond between the photo-labile unit and one of three components:
 a) a fragrance raw material unit thereby directly releasing a fragrance raw material;
 b) a pro-fragrance unit thereby instigating a sequence of one or more chemical transformations which release a fragrance raw material; or c) a linking group which further undergoes a sequence of one or more chemical transformations which subsequently release a fragrance raw material or pro-fragrance unit.

A first aspect of photo-labile units according to the present invention relate to units which are aryl acrylic acid units having the formula:

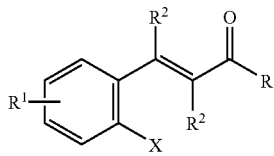

wherein R is a fragrance raw material or a unit capable of releasing a fragrance raw material; each $R^1$ is independently hydrogen, a unit which can substitute for hydrogen, $C_1$–$C_{12}$ substituted or unsubstituted hydrocarbyl unit, each $R^2$ is independently hydrogen, $C_1$–$C_{12}$ substituted or unsubstituted hydrocarbyl unit, and mixtures thereof; X is selected from the group consisting of —OH, —OC(O)$R^{12}$, —OC(O)O$R^{12}$, —NH$R^{12}$, and mixtures thereof; $R^{12}$ is H, $C_1$–$C_{12}$ substituted or unsubstituted alkyl, and mixtures thereof. These units are capable of releasing a fragrance raw material unit, a pro-fragrance unit, or a linking group bonded fragrance raw material unit or pro-fragrance unit; the photo-fragment compound having the formula:

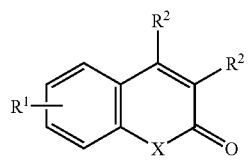

which can optionally be a fragrance raw material itself, inter alia, coumarin.

Non-limiting examples of photo-labile units included in this first aspect include a pro-fragrance wherein X is —NH$_2$, the $R^1$ unit is hydroxy, and both $R^2$ units are hydrogen which relates to 3-(2-amino-4-hydroxyphenyl)-acrylamide fragrance raw materials having the formula:

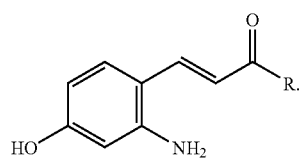

Another example relates to photo-labile units having the formula:

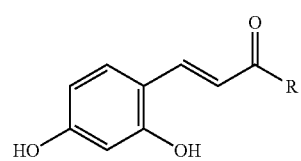

wherein both $R^1$ and X are hydroxyl.

A second aspect of the present invention relates to a photo-labile pro-fragrance conjugates having the formula:

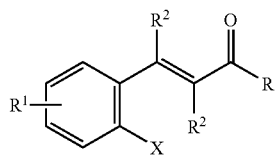

wherein $R^1$ is one or more electron donating groups; non-limiting examples of which include hydroxy, $C_1$–$C_{12}$ linear or branched alkoxy, —N($R^{12}$)$_2$, and mixtures thereof; $R^{12}$ is H, $C_1$–$C_{12}$ alkyl, and mixtures thereof, and the like.

A third aspect of the photo-labile units relates to aryl units having the formula:

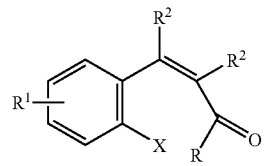

A fourth aspect of the photo-labile units relates to aryl units having the formula:

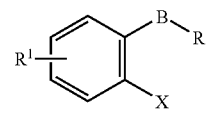

wherein B is a photo-labile unit which reactivity is enhanced or modulated by the aryl unit which comprises the balance of the photo-labile component. One embodiment of this aspect relates to silicon atom comprising units having the formula:

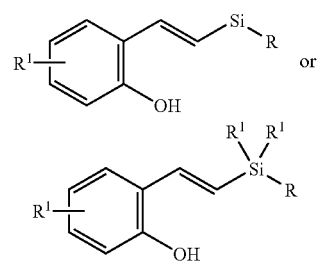

wherein $R^1$ is the same as defined herein above. Further non-limiting examples of embodiments of this aspect of the photo-labile units include compounds having the formula:

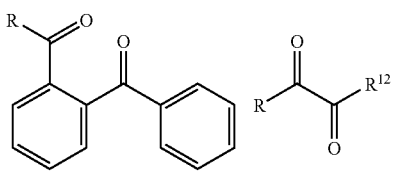

-continued

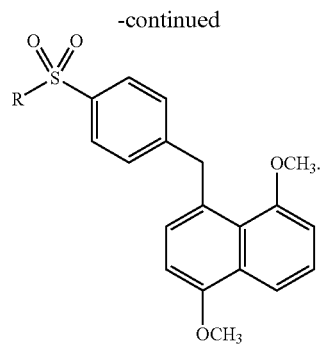

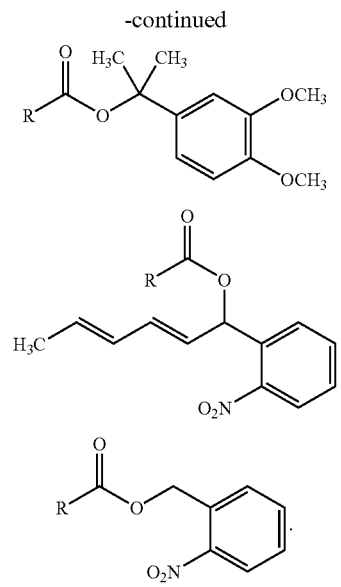

Linking Units

Depending upon the structure of the photo-labile unit and the rate at which the formulator desires the final fragrance raw material to be released, the use of an optional linking unit, L, may be desired or necessary. An example of a compound having an L unit present has the formula:

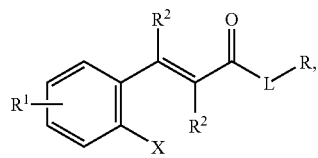

one embodiment of which has the formula:

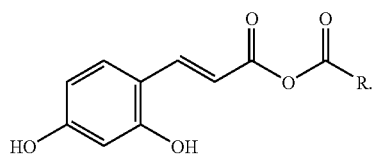

One aspect of the present invention relates to L units which are —OC(O)—, —NR$^3$C(O)—, —OC(R$^3$R$^4$)—, and —C(O)— carbonyl units. However, any suitable unit which facilitates the breakdown of the released pro-fragrance can serve as a linking unit in the photo-activated pro-fragrance conjugates of the present invention.

When the pro-fragrance unit is released from the photo-labile unit when a linker unit is present, the release of the photo-fragment compound and pro-fragrance or fragrance compound is accompanied by the release of a linker compound. For example, when the L unit is —OC(O)—, the linker compound is CO2.

When the L unit is —OC(R$^3$R$^4$)— the linker compound released can be an aldehyde or a ketone. In one aspect of the present invention, the aldehyde or ketone released is a perfume raw material.

Non-limiting examples of photo-activated compounds comprising an L unit include:

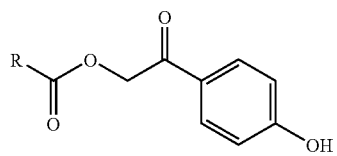

Pro-fragrance Units

Pro-fragrance units are released from the parent conjugate molecules when the conjugate is fragmented by a photo-chemical reaction. The pro-fragrance units of the present invention are attached to the photo-labile units either directly or by way of an optional linking unit, L.

As will be understood by the formulator, not all fragrance raw materials can be released from the same form of pro-fragrance. The two primary aspects of the present invention as it relates to release of a pro-fragrance unit are determined by the type of reaction which ultimately releases the final fragrance raw material.

The first aspect relates to type A release which involves a retro-Michael reaction, and the second aspect relates to type B release which involves a hydrolysis reaction.

Type A Release

The first aspect of the pro-fragrance unit component of the present invention relates to the release of fragrance raw material precursors which undergo a retro-Michael reaction.

Without wishing to be limited by theory, the reaction cascade which releases the fragrance raw material via retro-Michael reaction is believed to proceed according to the general scheme as depicted below for the release of a α,β-unsaturated ketone, inter alia, damascone.

1. A first photo-isomerization step:

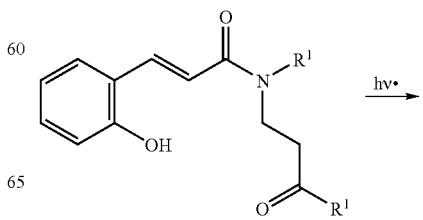

-continued

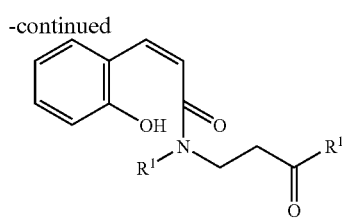

2. A second pro-fragrance unit elimination step:

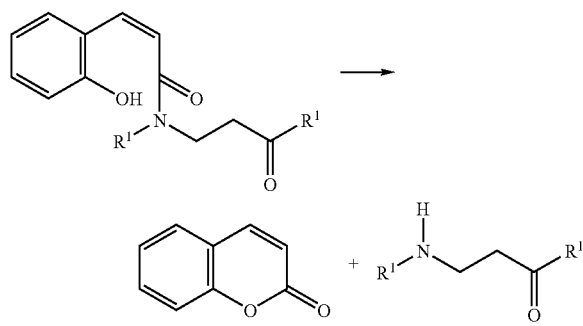

3. A third retro-Michael elimination step:

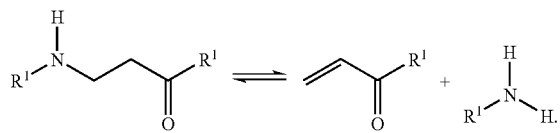

The pro-fragrances which comprise this aspect of the present invention have the formula:

wherein each $R^3$ is independently hydrogen, substituted or unsubstituted $C_1$–$C_{30}$ hydrocarbyl, and mixtures thereof.

One embodiment of this aspect of the present invention relates to pro-fragrances having the formula:

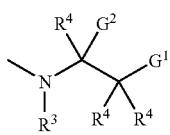

wherein each $R^4$ is independently selected from the group consisting of:
 i) hydrogen;
 ii) $C_1$–$C_{22}$ substituted or unsubstituted, branched or unbranched alkyl;
 iii) $C_2$–$C_{22}$ substituted or unsubstituted, branched or unbranched alkenyl;
 iv) $C_2$–$C_{20}$ substituted or unsubstituted, branched or unbranched hydroxyalkyl;

v) $C_7$–$C_{20}$ substituted or unsubstituted alkylenearyl;
 vi) $C_3$–$C_{20}$ substituted or unsubstituted cycloalkyl;
 vii) $C_6$–$C_{20}$ aryl;
 viii) $C_5$–$C_{20}$ heteroaryl units comprising one or more heteroatoms selected from the group consisting of nitrogen, oxygen, sulfur, and mixtures thereof;
 ix) two $R^4$ units can be taken together to form one or more aromatic or non-aromatic, heterocyclic or non-heterocyclic, single rings, fused rings, bicyclo rings, spiroannulated rings, or mixtures thereof, said rings comprising from 3 to 20 carbon atoms and one or more heteroatoms selected from the group consisting of nitrogen, oxygen, sulfur, and mixtures thereof;
 x) and mixtures thereof;

$G^1$ and $G^2$ are each independently hydrogen, $C_1$–$C_{20}$ linear or branched hydrocarbyl, —Y, —C(O)Y, and mixtures thereof; Y is $C_6$–$C_{10}$ substituted or unsubstituted cyclic alkyl. Non-limiting examples of embodiments of Y include 2,6,6-trimethylcyclohex-2-enyl, 2,6,6-trimethylcyclohex-1-enyl, 2,6,6-trimethylcyclohex-1-enyl, 2,6,6-trimethylcyclohex-3-enyl, and the like.

Another embodiment of this aspect of the present invention relates to pro-fragrances having the formula:

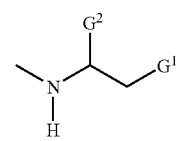

wherein $G_1$ and $G^2$ are each independently —$CH_3$, —C(O)$CH_3$, —Y, —C(O)Y, and mixtures thereof; Y is selected from the group consisting of:
 i) 2,6,6-trimethylcyclohex-2-enyl having the formula:

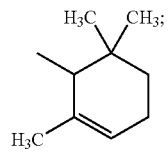

ii) 2,6,6-trimethylcyclohex-1-enyl having the formula:

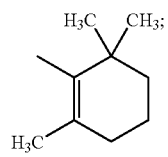

iii) 2,6,6-trimethylcyclohex-1-enyl having the formula:

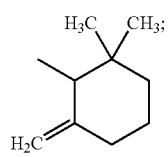

iv) 2,6,6-trimethylcyclohex-3-enyl having the formula:

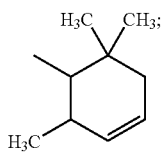

v) and mixtures thereof.

The following is a non-limiting example of a photo-labile pro-fragrance which releases a fragrance raw material (δ-damascone) via retro-Michael elimination.

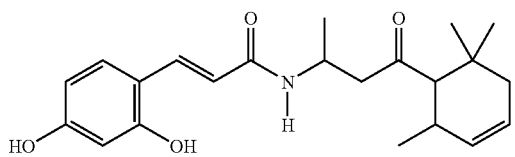

The following is a non-limiting example of a photo-labile pro-fragrance which comprises a linking unit and which releases a fragrance raw material (δ-damascone) via retro-Michael reaction.

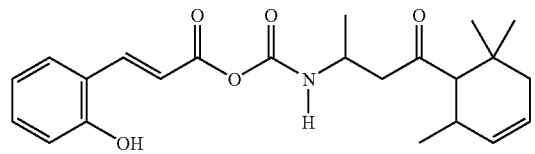

However, $R^3$ units in another aspect of the present invention can be taken together with an $R^1$ or $R^2$ unit of the photo-labile unit or with an L unit to form a $C_2$–$C_6$ heterocyclic ring for example, the conjugate having the formula:

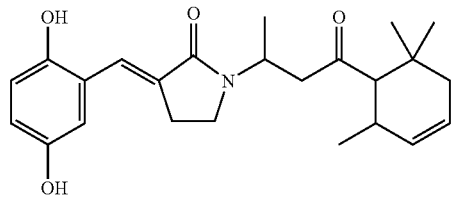

which is capable of releasing damascone and a photo-fragment compound having the proposed formula:

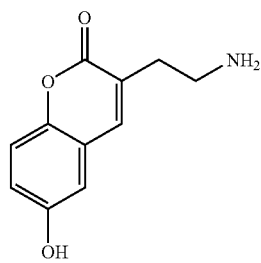

Type B Release

The second aspect of the pro-fragrance unit component of the present invention relates to the release of fragrance raw material precursors which undergo a hydrolysis step in the cascade releasing the fragrance raw material.

Without wishing to be limited by theory, the reaction cascade which releases the fragrance raw material via hydrolysis reaction is believed to proceed according to the general scheme as depicted below for the release of an aldehyde, inter alia, citral.

1. A first photo-isomerization step:

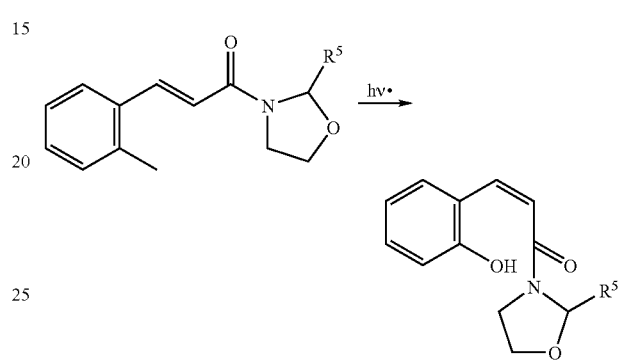

2. A second pro-fragrance unit elimination step:

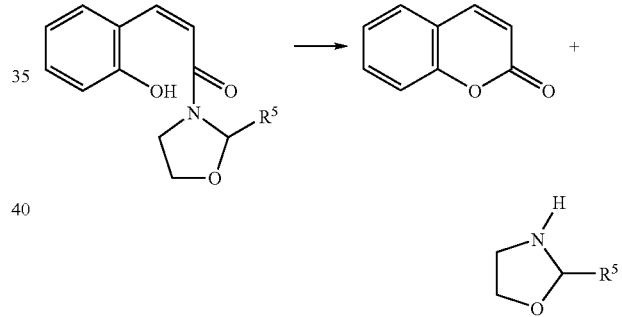

3. A third hydrolysis step:

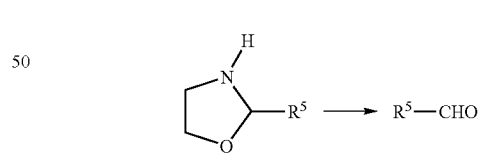

However, the above scheme only illustrates the general case of pro-fragrances which are in the form of oxazolidinones or oxazines having the formula:

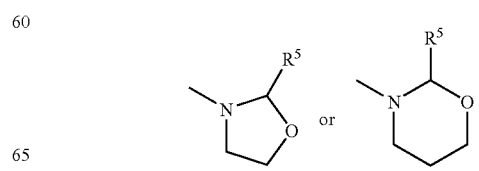

each of which is capable of releasing an aldehyde having the formula R⁵CHO.

However, the heterocyclic ring embodiment which comprises the pro-fragrance units of the present invention which have the general formula:

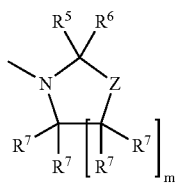

wherein Z is oxygen or sulfur; in one embodiment comprising oxazolidines, Y is oxygen and the index m is 1.

$R^5$ and $R^6$ units are selected such that upon hydrolysis of the pro-fragrance compound, aldehyde or ketone fragrance raw materials are released.

When an aldehyde is released $R^6$ is hydrogen.

As stated herein above, $R^5$ units can be any substituted or unsubstituted hydrocarbyl unit, non-limiting examples of which include $R^5$ units which comprise:
a) $C_6$–$C_{22}$ substituted or unsubstituted linear alkyl; $C_6$–$C_{12}$ alkyl when aliphatic aldehydes are released, inter alia, hexanal, octanal, nonanal, decanal, undecanal, and dodecanal;
b) $C_6$–$C_{22}$ substituted or unsubstituted branched alkyl; 2-methyldecanal, 2-methylundecanal;
c) $C_6$–$C_{22}$ substituted or unsubstituted linear alkenyl; $C_6$–$C_{12}$ alkenyl when unsaturated linear aldehydes are released, inter alia, trans-4-hexenal, cis-4-heptenal, and 10-undecenal;
d) $C_6$–$C_{22}$ substituted or unsubstituted branched alkenyl; $C_9$ or $C_{14}$ branched alkyl when the released aldehyde is a terpene or sesquiterpene aldehyde, inter alia, citronellal, citral;
e) $C_6$–$C_{22}$ substituted or unsubstituted cycloalkyl; $C_9$ or $C_{11}$ alkyl substituted cycloalkyl when the released ketone is cyclic terpenoid, inter alia α, β, γ, and δ ionone or damascone;
f) $C_6$–$C_{22}$ substituted or unsubstituted branched cycloalkyl;
g) $C_6$–$C_{22}$ substituted or unsubstituted cycloalkenyl;
h) $C_6$–$C_{22}$ substituted or unsubstituted branched cycloalkenyl;
i) $C_6$–$C_{22}$ substituted or unsubstituted aryl;
j) $C_6$–$C_{22}$ substituted or unsubstituted heterocyclicalkyl;
k) $C_6$–$C_{22}$ substituted or unsubstituted heterocyclicalkenyl;
l) and mixtures thereof;

$R^6$ units comprise:
a) hydrogen;
b) $C_1$–$C_{10}$ substituted or unsubstituted linear alkyl; as in the case of methyl ketones, inter alia, α, β, γ, and δ ionone;
c) $C_3$–$C_{10}$ substituted or unsubstituted branched alkyl; for example, tagetone wherein R is 2-methyl-1,3-dieneyl and $R^1$ is isobutyl;
d) $C_2$–$C_{10}$ substituted or unsubstituted linear alkenyl; as in the case of α, β, γ, and δ damascone;
e) $C_3$–$C_{10}$ substituted or unsubstituted branched alkenyl;
f) $C_3$–$C_{15}$ substituted or unsubstituted cycloalkyl;

g) $C_4$–$C_{15}$ substituted or unsubstituted branched cycloalkyl;
h) $C_4$–$C_{15}$ substituted or unsubstituted cycloalkenyl;
i) $C_5$–$C_{15}$ substituted or unsubstituted branched cycloalkenyl;
j) $C_6$–$C_{15}$ substituted or unsubstituted aryl;
k) $C_6$–$C_{22}$ substituted or unsubstituted heterocyclicalkyl;
l) $C_6$–$C_{22}$ substituted or unsubstituted heterocyclicalkenyl;
m) and mixtures thereof;

alternatively the $R^5$ and $R^6$ units can be taken together to form a substituted or unsubstituted ring having in the ring from 3 to 10 carbon atoms; for example, $R^5$ and $R^6$ taken together can be fused ring comprising ketones, inter alia, nootkatone; or mono-cyclic ketones, inter alia, menthone, isomenthone, carvone, and fenchone.

For the hydrolyzable ring pro-fragrances of the present invention each $R^7$ is independently selected from any substituted or unsubstituted hydrocarbyl unit, non-limiting embodiments are selected from the group consisting of:
a) $R^6$;
b) hydroxyl;
c) a carbonyl comprising unit having the formula:

—(CH₂)ₓCOR⁸ wherein $R^8$ is:
i) —OH;
ii) —OR⁹ wherein $R^9$ is hydrogen, $C_1$–$C_{15}$ substituted linear alkyl, $C_{11}$–$C_{15}$ unsubstituted linear alkyl, $C_1$–$C_{15}$ substituted branched alkyl, $C_{11}$–$C_{15}$ unsubstituted branched alkyl, $C_2$–$C_{22}$ substituted or unsubstituted linear alkenyl, $C_3$–$C_{22}$ substituted or unsubstituted branched alkenyl, or mixtures thereof, wherein said substitution is not halogen or thioalkyl; $R^9$ is methyl, $R^9$ is hydrogen and Z is oxygen or sulfur when an oxazolidine is formed from the methyl esters of serine, threonine, cysteine, and the like;
iii) —N(R¹⁰)₂ wherein $R^{10}$ is hydrogen, $C_1$–$C_6$ substituted or unsubstituted linear alkyl, $C_3$–$C_6$ substituted or unsubstituted branched alkyl, or mixtures thereof;
iv) $C_1$–$C_{22}$ substituted or unsubstituted linear alkyl;
v) $C_1$–$C_{22}$ substituted or unsubstituted branched alkyl;
vi) $C_2$–$C_{22}$ substituted or unsubstituted linear alkenyl;
vii) $C_3$–$C_{22}$ substituted or unsubstituted branched alkenyl;
viii) $C_3$–$C_{22}$ substituted or unsubstituted cycloalkyl;
ix) $C_6$–$C_{22}$ substituted or unsubstituted aryl;
x) $C_6$–$C_{22}$ substituted or unsubstituted heterocyclicalkyl;
xi) $C_6$–$C_{22}$ substituted or unsubstituted heterocyclicalkenyl;
the index x is from 0 to 22;
d) alkyleneoxy units having the formula:

—[C(R¹¹)₂]ᵧ[C(R¹¹)₂C(R¹¹)₂O]ᵤR¹¹ wherein each $R^{11}$ is independently;
i) hydrogen;
ii) —OH;
iii) $C_1$–$C_4$ alkyl;
iv) or mixtures thereof;
two $R^{11}$ units can be taken together to form a $C_3$–$C_6$ spiroannulated ring, carbonyl unit, or mixtures thereof; y has the value from 0 to 10, z has the value from 1 to 50;
e) and mixtures thereof;

any two R⁷ units can be taken together to form:
  i) a carbonyl moiety;
  ii) a $C_3$–$C_6$ spiroannulated ring;
  iii) a heterocyclic aromatic ring comprising from 5 to 7 atoms;
  iv) a non-heterocyclic aromatic ring comprising from 5 to 7 atoms;
  v) a heterocyclic ring comprising from 5 to 7 atoms;
  vi) a non-heterocyclic ring comprising from 5 to 7 atoms;
  vii) or mixtures thereof; and the index m is an integer from 1 to 3.

For example, each of the ring carbon atoms may have one or both of the hydrogen atoms substituted as defined herein above or taken together to form an aromatic or non-aromatic, carbocyclic or heterocyclic ring, for example:

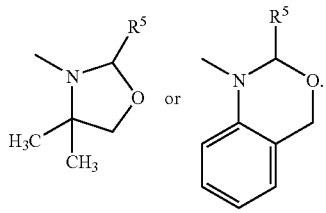

One iteration of this embodiment relates to oxazolidines having the formula:

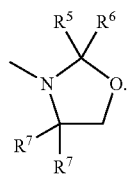

wherein $R^6$ is selected from the group consisting of hydrogen and methyl; each $R^7$ is independently hydrogen, methyl, —C(O)OR⁹ and mixtures thereof; $R^9$ is hydrogen, $C_1$–$C_{12}$ alkyl, and mixtures thereof.

The following is a non-limiting example of the oxazolidone embodiment of the present invention.

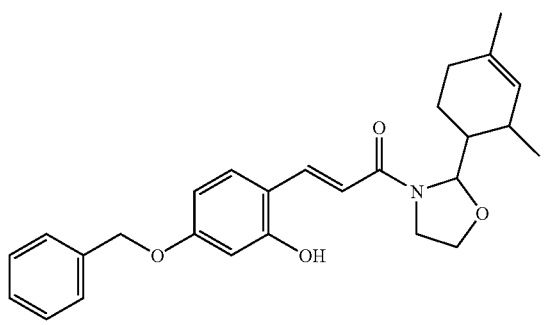

Hydrolysis based release of the fragrance raw material can proceed by way of any hydrolyzable pro-fragrance compound which is initiated by the release of the pro-fragrance unit from a photo-labile pro-fragrance conjugate. For example, the ionone series of ketone fragrance raw materials, unlike the damascone series delivered by Type A Release, are formed into photo-labile pro-fragrance conjugates in which the photo-labile unit is connected to a pro-fragrance unit consisting of a pro-fragrance compound that is an imine or an enamine that are themselves formed from the reaction of an aldehyde or ketone fragrance raw material with an amine compound. The imine- or iminium-based pro-fragrance compounds are released upon activation of the conjugate. The following is an example of a photo-labile pro-fragrance conjugate that is capable of releasing an enamine-based pro-fragrance compound of the present invention.

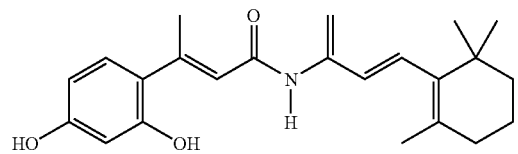

The Type B Release photo-activated pro-fragrances can also comprise a suitable linking group for example a compound having the formula:

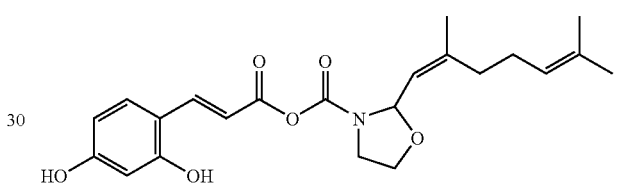

Another type of Type B Release relates to aminals or ketals having, for example, the formula:

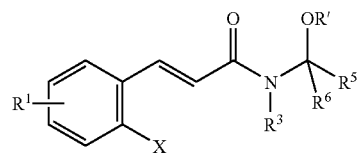

which is capable of releasing an aldehyde or ketone fragrance raw material having the formula $R^5CHO$ or $R^5R^6CHO$ and an alcohol having the formula R'OH. R'OH can be a fragrance raw material or not a fragrance raw material depending on the needs of the formulator. A non-limiting example of an aminal according to the present invention has the formula:

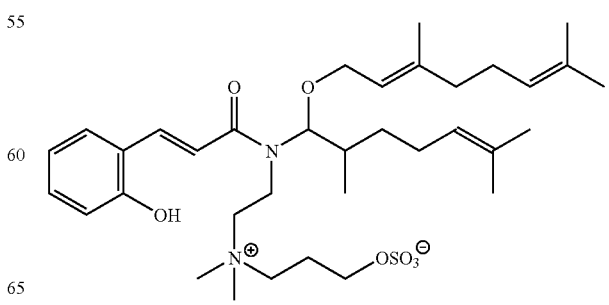

The formulator when using aminals to deliver two fragrance raw materials can make use of the $R^3$ nitrogen unit to control the release rate of the fragrance raw materials once the photo-labile unit has released the pro-fragrance component. The formulator can make use of the $R^3$ nitrogen unit to control the physical properties of the photo-labile pro-fragrance conjugate. Such properties include, but are not limited to, the ability of the conjugate to deposit on a desired surface in an aqueous wash environment.

A further example of Type B Release relates to conjugates which are activated by the breaking of the bond between the photo-labile unit and the pro-fragrance unit, wherein an intramolecular reaction ensues which displaces a pro-fragrance compound which then hydrolyzes to release the fragrance raw material. A non-limiting general example is the amino-amide photo-labile pro-fragrance conjugate depicted in the scheme below:

1. A photo-isomerization followed by a pro-fragrance compound elimination step:

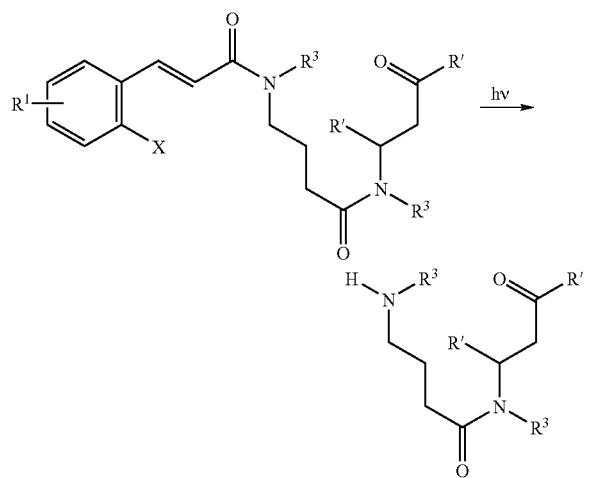

2. A subsequent cyclization step:

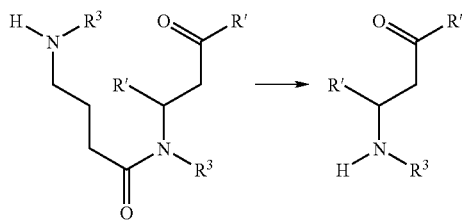

3. A final elimination step:

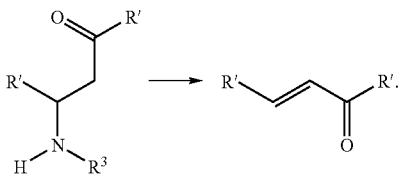

Fragrance Raw Materials

Mixtures of fragrance materials are known by those skilled in the art of fragrances and perfumes as "accords".

The term "accord" as used herein is defined as "a mixture of two or more 'fragrance raw materials' which are artfully combined to impart a pleasurable scent, odor, essence, or fragrance characteristic". For the purposes of the present invention "fragrance raw materials" are herein defined as compounds having a molecular weight of at least 100 g/mol and which are useful in imparting an odor, fragrance, essence, or scent either alone or in combination with other "fragrance raw materials". For the purposes of the present invention, fragrance raw materials which comprise an amino unit can be directly attached to the photo-labile unit and, therefore, released directly without further reaction.

Typically "fragrance raw materials" comprise inter alia alcohols, ketones, aldehydes, esters, ethers, nitrites, and alkenes such as terpenes. A listing of common "fragrance raw materials" can be found in various reference sources, for example, "Perfume and Flavor Chemicals", Vols. I and II; Steffen Arctander Allured Pub. Co. (1994) and "Perfumes: Art, Science and Technology"; Müller, P. M. and Lamparsky, D., Blackie Academic and Professional (1994) both incorporated herein by reference.

Examples of fragrance raw material ketones which are capable of being released by the compounds of the present invention include 1-(2,6,6-trimethylcyclohex-2-enyl)-2-butene-1-one (α-damascone), 1-(2,6,6-trimethyl-cyclohex-1-enyl)-2-butene-1-one (β-damascone), 1-(2-methylene-6,6-dimethyl-cyclohexanyl)-2-butene-1-one (γ-damascone), 1-(2,6,6-trimethylcyclohex-3-enyl)-2-butene-1-one (δ-damascone), 4-(2,6,6-trimethylcyclohex-2-enyl)-3-butene-2-one (α-ionone), 4-(2,6,6-trimethylcyclohex-1-enyl)-3-butene-2-one (β-ionone), 4-(2-methylene-6,6-dimethylcyclo-hexanyl)-3-butene-2-one (γ-ionone).

Aldehydes which are releasable from the photo-activated conjugates of the present invention include but are not limited to phenylacetaldehyde, p-methyl phenylacetaldehyde, p-isopropyl phenylacetaldehyde, methylnonyl acetaldehyde, phenylpropanal, 3-(4-t-butylphenyl)-2-methyl propanal, 3-(4-t-butylphenyl)-propanal, 3-(4-methoxyphenyl)-2-methylpropanal, 3-(4-isopropylphenyl)-2-methylpropanal, 3-(3,4-methylenedioxyphenyl)-2-methylpropanal, 3-(4-ethylpheny)-2,2-dimethylpropanal, phenylbutanal, 3-methyl-5-phenylpentanal, hexanal, trans-2-hexenal, cis-hex-3-enal, heptanal, cis-4-heptenal, 2-ethyl-2-heptenal, 2,6-dimethyl-5-heptenal, 2,4-heptadienal, octanal, 2-octenal, 3,7-dimethyloctanal, 3,7-dimethyl-2,6-octadien-1-al, 3,7-dimethyl-1,6-octadien-3-al, 3,7-dimethyl-6-octenal, 3,7-dimethyl-7-hydroxyoctan-1-al, nonanal, 6-nonenal, 2,4-nonadienal, 2,6-nonadienal, decanal, 2-methyl decanal, 4-decenal, 9-decenal, 2,4-decadienal, undecanal, 2-methyldecanal, 2-methylundecanal, 2,6,10-trimethyl-9-undecenal, undec-10-enyl aldehyde, undec-8-enanal, dodecanal, tridecanal, tetradecanal, anisaldehyde, bourgenonal, cinnamic aldehyde, α-amylcinnam-aldehyde, α-hexyl cinnamaldehyde, methoxy-cinnamaldehyde, citronellal, hydroxy-citronellal, isocyclocitral, citronellyl oxyacet-aldehyde, cortexaldehyde, cumminic aldehyde, cyclamen aldehyde, florhydral, heliotropin, hydrotropic aldehyde, lilial, vanillin, ethyl vanillin, benzaldehyde, p-methyl benzaldehyde, 3,4-dimethoxybenzaldehyde, 3- and 4-(4-hydroxy-4-methyl-pentyl)-3-cyclohexene-1-carboxaldehyde, 2,4-dimethyl-3-cyclohexene-1-carboxaldehyde, 1-methyl-3-(4-methylpentyl)-3-cyclohexencarboxaldehyde, p-methylphenoxyacetaldehyde, and mixtures thereof.

Fragrance raw materials suitable for use in the present invention are described in U.S. Pat. No. 5,919,752 Morelli et al., issued Jul. 6, 1999; U.S. Pat. No. 6,013,618 Morelli et al., issued Jan. 11, 2000; U.S. Pat. No. 6,077,821 Morelli et al., issued Jun. 20, 2000; U.S. Pat. No. 6,087,322 Morelli et al., issued Jul. 11, 2000; U.S. Pat. No. 6,114,302 Morelli et al., issued Sep. 5, 2000; U.S. Pat. No. 6,177,389 Morelli et al., issued Jan. 23, 2001; all of which are incorporated herein by reference.

Odor Detection Threshold

For the purposes of the present invention the term "odor detection threshold" is defined as the level at which a fragrance raw material is perceptible to the average human. The odor detection threshold (ODT) of the compositions of the present invention are preferably measured by carefully controlled gas chromatograph (GC) conditions as described hereinbelow.

Determination of Odor Detection Thresholds is as follows. A gas chromatograph is characterized to determine the exact volume of material injected by a syringe, the precise split ratio, and the hydrocarbon response using a hydrocarbon standard of known concentration and chain-length distribution. The airflow rate in accurately measured and, assuming the duration of a human inhalation to last 0.02 minutes, the sampled volume is calculated. Since the precise concentration at the detector at any point in time is known, the mass per volume inhaled is known and hence the concentration of material. To determine whether a material has a threshold below 10 ppb, solutions are delivered to the sniff port at the back-calculated concentration. A panelist sniffs the GC effluent and identifies the retention time when odor is notice. The average over all panelists determines the threshold of noticeability or ODT. The necessary amount of analyte is injected onto the column to achieve a 10 ppb concentration at the detector. Typical gas chromatograph parameters for determining odor detection thresholds are listed below.

GC: 5890 Series II with FID detector 7673 Auto sampler
Column: J&W Scientific DB-1, length 30 m, i.d. 0.25 mm, film thickness 1 □m.
Split Injection: 17/1 split ratio
Autosampler: 1.13 □l/injection
Column flow: 1.10 mL/min
Air flow: 345 mL/min
Inlet temperature: 245° C.
Detector temperature: 285° C.
Temperature Information:
　Initial temperature: 50° C.
　Rate: 5° C./min
　Final temperature: 280° C.
　Final time: 6 min
Leading assumptions: 0.02 minutes per sniff and that GC air adds to sample dilution.

A general first procedure relates to the conversion of a starting material having formula 1 to the aryl acrylamide photo-labile pro-fragrance 3 by way of the intermediate aryl acrylic acid 2 as depicted in the following scheme:

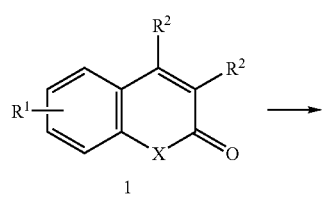

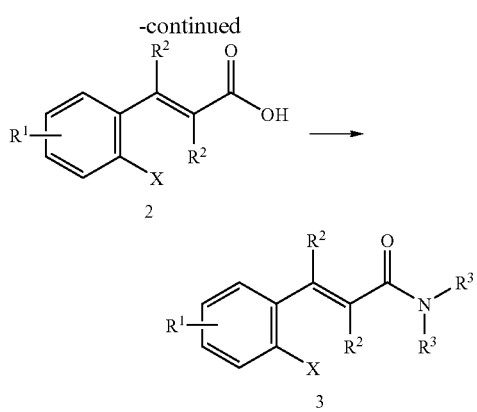

In the case wherein X is equal to oxygen (coumarin derivatives) the preparation begins with a von Pechmann condensation as in the example of the reaction of resorcinol with acetoacetic acid ethyl ester depicted in the following scheme:

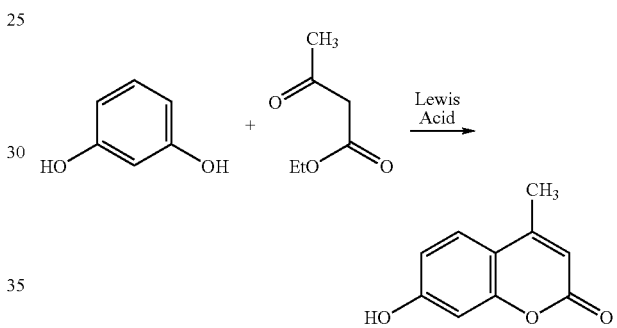

Coumarin syntheses are reviewed by Dean, F. M. "Naturally Occurring Oxygen Ring Compounds"; Butterworths: London, 1963; p. 176.

Preparation of 3-(2,4-dihydroxy-phenyl)-acrylic acid (5) from 7-hydroxy-chromen-2-one (4):

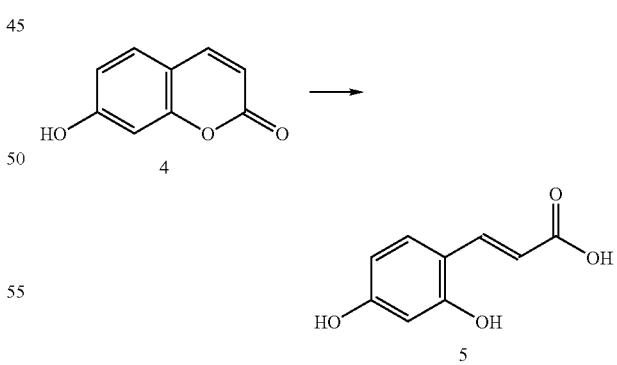

To a solution of 20% sodium sulfite (640 g) at 60° C. is added 7-hydroxy-chromen-2-one (75.0 g, 0.416 mol). The reaction mixture is warmed to 100° C. and stirred for 1.5 h. To this solution is added dropwise 30% KOH solution (301 g). The stirred mixture is cooled to 0° C. and acidified by the slow and careful addition of concentrated HCl, keeping the solution temperature below 10° C. The colorless precipitate is separated by filtration, washed with water and dried for 12 h under vacuum at 45° C. The resulting 3-(2,4-dihydroxy-phenyl)-acrylic acid is a colorless solid (24.0 g) and is used without further purification.

EXAMPLE 1

Preparation of triplal oxazolidine conjugate (7)

Step (1) Preparation of 2-(2,4-Dimethyl-cyclohex-3-enyl)-oxazolidine (6):

To a 0° C. stirred solution of 66 g (0.47 mol) triplal and 21 g sodium sulfate in 150 mL of methanol is added 29 g (0.47 mol) of ethanolamine. The reaction is allowed to warm to room temperature. After stirring for 24 h the mixture is cooled to 0° C. and the solids are removed via vacuum filtration through Celite. Evaporation of the solvent gives a clear, slightly yellow oil.

Step (2) Preparation of 1-[2-(2,4-Dimethyl-cyclohex-3-enyl)-oxazolidin-3-yl]-3-(2-hydroxy-phenyl)-propenone (7):

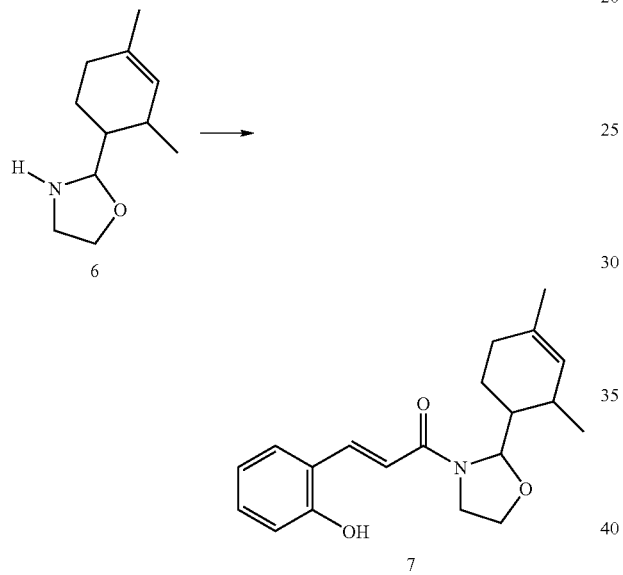

To a 0° C. solution of 8.2 g (0.050 mol) of o-hydroxy-trans-cinnamic acid in 500 mL of anhydrous tetrahydrofuran (THF) is added 10.3 g (0.050 mol) of 1,3-dicyclohexylcarbodiimide (DCC). After stirring for 10 min, 6.8 g (0.050 mol) of 1-hydroxybenzotriazole (HOBt), 8.2 g (0.045 mol) of 2-(2,4-dimethyl-3-cyclohexen-1-yl)-1,3-oxazolidine and 1.1 g (0.009 mol) of 4-(dimethylamino)pyridine (DMAP) is added and stirred at 0° C. for 1 h, warmed to room temperature and stirred for an additional 24 h. The mixture is cooled to 0° C., filtered and the solvent is removed in vacuo. The residue is diluted with ethyl acetate and washed three times with saturated sodium bicarbonate, followed by 10% citric acid and brine. The organic layer is dried over anhydrous magnesium sulfate, filtered and concentrated in vacuo. The product 7 is further purified by flash chromatography on basic alumina with 20:1 chloroform/methanol.

EXAMPLE 2

Preparation of dihydro-β-ionone oxazine conjugate (9)

Step (1) Preparation of 2-Methyl-2-[2-(2,6,6-trimethyl-cyclohex-1-enyl)-ethyl]-[1,3]oxazinane (8):

To a 0° C. stirred solution of 4-(2,6,6-trimethyl-cyclohex-1-enyl)-butan-2-one (25.2 g, 0.13 mol) and sodium sulfate (20 g) in 80 mL of methanol is added 3-amino-1-propanol (10 g, 0.13 mol). The reaction is allowed to warm to room temperature. After stirring for 24 h the mixture is cooled to 0° C. and the solids are removed via vacuum filtration through Celite. Evaporation of the solvent gives a clear yellow oil.

Step (2) Preparation of 3-(2,4-Dihydroxy-phenyl)-1-{2-methyl-2-[2-(2,6,6-trimethyl -cyclohex-1-enyl)-ethyl]-[1,3]oxazinan-3-yl}-but-2-en-1-one (9):

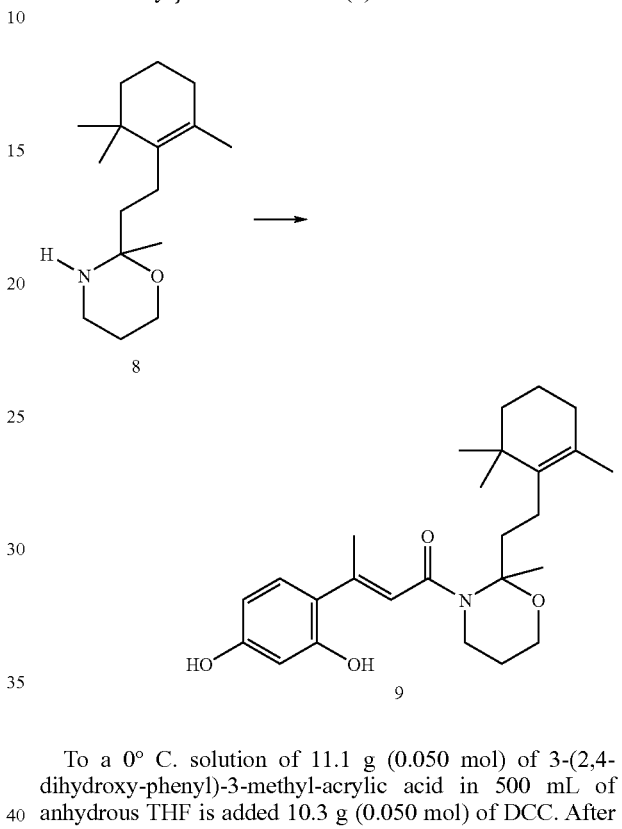

To a 0° C. solution of 11.1 g (0.050 mol) of 3-(2,4-dihydroxy-phenyl)-3-methyl-acrylic acid in 500 mL of anhydrous THF is added 10.3 g (0.050 mol) of DCC. After stirring for 10 min, 6.8 g (0.050 mol) of HOBt, 11.3 g (0.045 mol) of 2-methyl-2-[2-(2,6,6-trimethyl-cyclohex-1-enyl)-ethyl]-[1,3]oxazinane (8) and 1.1 g (0.009 mol) of DMAP are added and stirred at 0° C. for 1 h, warmed to room temperature and stirred for an additional 24 h. The mixture is cooled to 0° C., filtered and the solvent is removed in vacuo. The residue is diluted with ethyl acetate and washed three times with saturated sodium bicarbonate, followed by 10% citric acid and brine. The organic layer is dried over anhydrous magnesium sulfate, filtered and concentrated in vacuo. The product 9 is further purified by flash chromatography on basic alumina with 20:1 chloroform/methanol.

EXAMPLE 3

Preparation of δ-damascone Michael adduct conjugate (11)

Step (1) Preparation of 3-Amino-1-(2,6,6-trimethyl-cyclohex-3-enyl)-butan-1-one (10):

To a 0° C. stirred solution of 66.2 g (0.574 mol, 1.2 equiv) of 1-(2,6,6-trimethyl-cyclohex-3-enyl)-but-2-en-1-one (δ-damascone) in 250 mL of ethanol is added 143.3 mL (1 equiv, 0.287 mol) of ammonia (Aldrich, 2.0 M in ethanol). The reaction is allowed to warm to room temperature. After stirring for 24 h, the ethanol is concentrated by rotary evaporation to give an oil consisting of 10.

Step (2) Preparation of 3-(2,4-Dihydroxy-phenyl)-N-[1-methyl-3-oxo-3-(2,6,6-trimethyl-cyclohex-3-enyl)-propyl]-acrylamide (11)

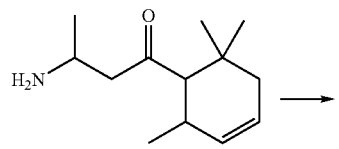

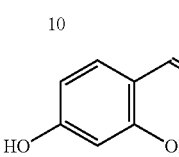

To a solution of 3-amino-1-(2,6,6-trimethyl-cyclohex-3-enyl)-butan-1-one (2.38, 11.3 mmol, 10) and triethylamine (2.30 g, 22.6 mmol) in anhydrous THF (150 mL) stirred for 5 min at 22° C. is added 3-(2,4-dihydroxyphenyl)-acrylic acid (2.04 g, 11.3 mmol). To this heterogeneous solution is added BOP Reagent (5.00 g, 11.3 mmol; Aldrich #22,608-4) in DMF (10 mL), and the subsequent homogeneous reaction mixture is stirred for 1 h. The reaction mixture is partitioned between ether (200 mL) and water (400 mL); the organic layer is removed and washed with ether (200 mL). The combined organic layers are washed sequentially with saturated sodium bicarbonate solution (200 mL) and brine (200 mL). The organic layer is dried over anhydrous magnesium sulfate, vacuum filtered and concentrated to give 3-(2,4-dihydroxy-phenyl)-acrylic acid 1,5-dimethyl-1-vinyl-hex-4-enyl ester as an oil that is purified by flash chromatography to give 11 as a colorless solid.

EXAMPLE 4

Preparation of bis-δ-damascone Michael adduct conjugate (15)

Step (1) To a 0° C. stirred solution of 96 g (0.50 mol) of 1-(2,6,6-trimethyl-cyclohex-3-enyl)-but-2-en-1-one (δ-damascone) in 250 mL of ethanol is added 47 g (0.25 mol) of $N^1$-[3-(3-Amino-propylamino)-propyl]-propane-1,3-diamine. The reaction is allowed to warm to room temperature. After stirring for 24 h, the ethanol is concentrated by rotary evaporation to give 3-[3-(3-{3-[1-methyl-3-oxo-3-(2,6,6-trimethyl-cyclohex-3-enyl)-propylamino]-propylamino}-propylamino)-propylamino]-1-(2,6,6-trimethyl-cyclohex-3-enyl)-butan-1-one (bis-Michael adduct 14) as an oil.

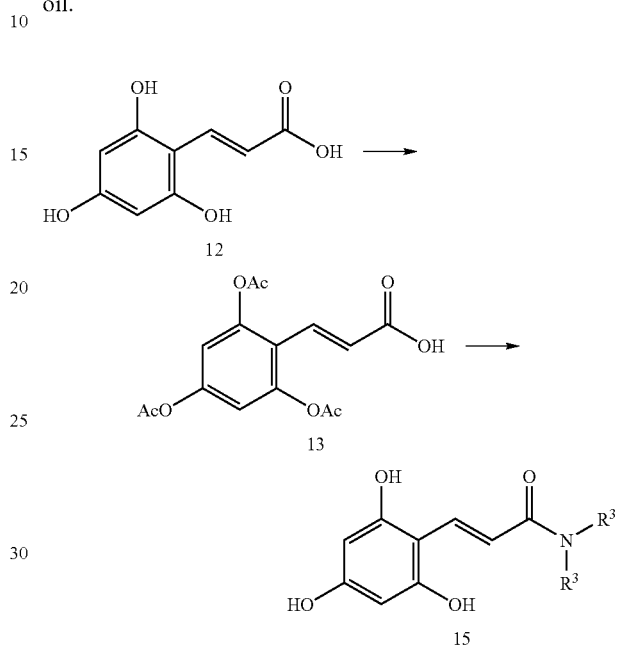

Step (2) which is conversion of starting material 12 to intermediate 13 can be a accomplished by the method described in *Synthetic Comm.* 1991, 21, 351 included herein by reference.

Step (3) conversion of intermediate 13 to 15.

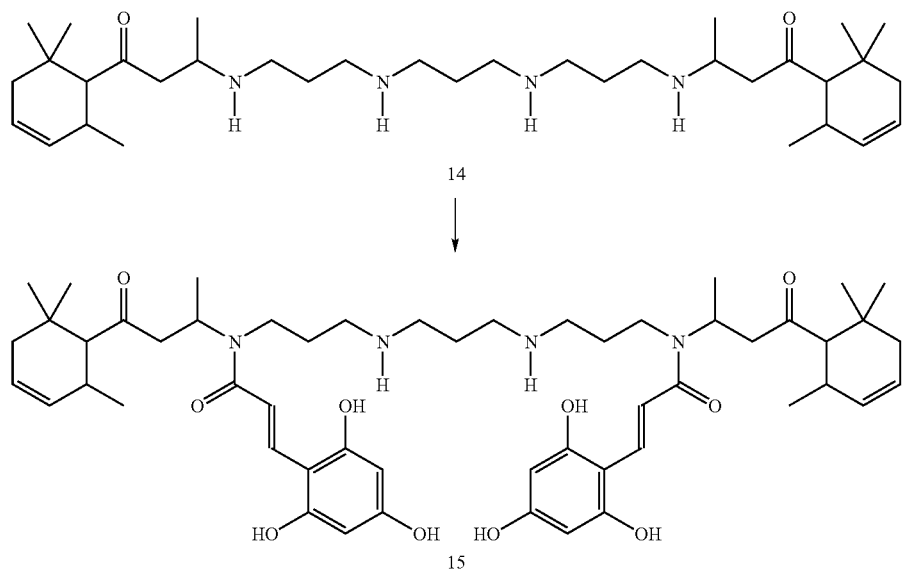

A solution of intermediate 13 (1.2 g, 3.7 mmol), thionyl chloride (2 equiv, 0.88 g, 7.4 mmol, 0.54 mL) in anhydrous toluene (50 mL) is refluxed for 3 h under an inert atmosphere. The reaction mixture is evaporated to dryness under vacuum and to the crude acid chloride is added another portion of toluene (50 mL). Bis-Michael adduct 14 (1.1 g, 1.9 mmol) is added and the reaction mixture is allowed to stir for 12 h. The mixture is diluted with toluene (100 mL) and washed with 100 mL portions of 1 N HCl, water and brine. The organic layer is dried over anhydrous magnesium sulfate, filtered and concentrated to give acyl-protected 15. Removal of the acetoxy units by the method of *Synthetic Comm.* 1991, 21, 351, incorporated herein by reference, affords 15.

FORMULATIONS

The present invention relates to a photo-labile fragrance delivery system which delivers a photo-labile pro-fragrance conjugate. The pro-fragrance relies upon the photo-initiated cascade to deliver the fragrance raw material. Because it is not necessary that the pro-fragrance compound immediately begins releasing an aldehyde or ketone once the photo-labile unit has released said pro-fragrance compound, the formulator may form a wide array of delivery systems. In general, the systems of the present invention comprise several embodiments having various ranges of pro-fragrance conjugate, for example:

a) from about 0.001% to about 5%, another embodiment comprises from about 0.005% to about 1%, a range of from about 0.01% to about 0.2% encompasses yet another embodiment, while a further embodiment comprises from about 0.02% to about 0.1% by weight, of a photo-activated pro-fragrance conjugate, said conjugate comprising:
  i) a photo-labile unit which upon exposure to electromagnetic radiation is capable of releasing a pro-fragrance unit as a pro-fragrance compound; and
  ii) a pro-fragrance compound, which when so released is capable of releasing a fragrance raw material; and Another aspect of the present invention relates to conjugates of the present invention that comprise a photo-labile pro-fragrance conjugate comprising a photo-labile unit which upon exposure to electromagnetic radiation is capable of releasing a pro-fragrance unit as a fragrance compound.

b) the balance carriers and adjunct ingredients.

The photo-labile pro-fragrances of the present invention have wide utility in perfumes and fine fragrances. This embodiment of the present invention comprises:

A) from about 0.001% by weight, of one or more photo-activated pro-fragrance conjugates, said conjugates each comprising:
  a) a photo-labile unit which upon exposure to electromagnetic radiation is capable of releasing a pro-fragrance unit;
  b) a pro-fragrance unit, which when so released is either
    i) a pro-fragrance compound capable of releasing a fragrance raw material; or
    ii) a fragrance raw material;
B) from about 0.01% to about 99% by weight, of an admixture of fragrance raw material; and
C) the balance carriers and adjunct ingredients.

Typically the carrier for fine fragrances and perfumes is ethanol or ethanol/water. In addition to the photo-labile conjugates of the present invention, other pro-fragrances, pro-accords, and the like can be included, especially species which take advantage of the differential pH of skin. For example, acid labile pro-fragrances include orthoesters, acetals, ketals, and the like. Therefore, the combination of a photo-labile pro-fragrance and an acid labile pro-fragrance which releases the same fragrance raw material, inter alia, damascone, citronellal, is one aspect encompassed by the present invention.

For the purposes of the present invention the terms "perfume" and "fine fragrance" are essentially synonymous and are used collectively or interchangeably throughout the present specification and are taken to mean the more concentrated forms of fragrance-containing compositions. Aspects of the present invention which apply to "perfumes" will therefore apply equally to "fine fragrances" and vice versa. Typically, colognes, eau de toilettes, after shaves, and other fragrance-containing embodiments are perfumes or fine fragrances which have a greater degree of dilution, usually by a volatile carrier such as ethanol.

EMBODIMENTS

The following are additional non-limiting embodiments of the present invention.

Skin Conditioning Lotions

An example of a skin care composition of the present invention comprises an ester having a total number of carbon atoms in excess of about 28, for example lauryl laurate, lauryl myristate, myristyl myristate, behenyl caprate, cetearyl palmitate, behenyl stearate, more preferably cetearyl palmitate and cetyl stearate.

The present compositions in addition to the esters described herein above, contain an emollient material in an amount such that the amount of ester plus emollient is from about 0.2%, preferably from about 4% to about 25%, preferably to about 18% of the total composition. One function of the emollient is to ensure that the ester is plasticized sufficiently to allow it to be in a film-like state on the skin. The emollient in the present compositions is selected from the group consisting of fatty alcohols, esters having fewer than about 24 total carbon atoms (e.g. isopropyl palmitate), branched chain esters having greater than about 24 total carbon atoms (e.g. cetearyl octonate), squalane, liquid or solid paraffins, mixtures of fatty acids and squalane, mixtures of fatty acids and liquid or solid paraffins and mixtures thereof. The aforementioned esters, those having fewer than 24 carbon atoms or branched and having more than 24 carbon atoms, if used as an emollient should preferably be used in an mount equal to about a third of the long chain ester. The particular emollient selected depends in part on the particular ester selected since proper plasticization, as indicated above, is desired. The emollient for the esters having more than 28 carbon atoms is preferably selected from the group consisting of squalane, liquid or solid paraffins and mixtures of fatty alcohols with squalane or paraffins. Typical fatty alcohols and fatty acids useful in the present compositions include those having from 12–22 carbon atoms such as cetyl alcohol, myristyl alcohol, stearyl alcohol, stearic acid and palmitic acid. Paraffins include, for example, mineral oil, petrolatum and paraffin wax. It is preferred that distilled water be used in the present compositions.

Optional Components

Oil Phase Components

In addition to the long chain esters, emollients and emulsifiers described previously, the oil phase of the present compositions may contain a variety of materials including:

(a) Esters not meeting the requirements for the long chain ester and not present as an emollient, supra, such as oleyl oleate, isostearyl isostearate, isopropyl lanolate, isopropyl myristate, butyl stearate, myristyl lactate and 2-ethyl hexyl palmitate;
(b) Oils such as castor oil, jojoba oil, cottonseed oil, peanut oil and sesame oil;
(c) Waxes such as ceresin wax, carnuba wax, beeswax and castor wax;
(d) Lanolin, its derivatives and components such as acetylated lanolin, lanolin alcohols and lanolin fatty acids. Lanolin fatty acids are described in U.S. Pat. No. Re. 29,814, Oct. 24, 1978 to W. E. Snyder incorporated herein by reference.
(e) Polyalkylenes such as hydrogenated polyisobutene and polyethylene; and
Sterols such as cholesterol and phytosterol.

These optional oil phase materials may comprise up to about 80% of the oil phase, preferably up to about 35%. When used at these levels, the optional components do not impair the occlusive nature of the compositions and add to the composition's total cosmetic performance.

Water Phase Components

The water phase of the compositions may contain many different materials including:
(a) Humectants, such as sorbitol, glycerine, propylene glycol, alkoxylated glucose and hexanetriol at a level of from about 1% to about 20%.
(b) Thickening agents such as carboxyvinyl polymers, ethyl cellulose, polyvinyl alcohol, carboxymethyl cellulose, vegetable gums and clays such as Veegum.RTM. (magnesium aluminum silicate, R. T. Vanderbilt, Inc.) at a level of from about 0.01% to about 6%;
(c) Proteins and polypeptides at a level of from about 0.1% to about 3%;
(d) Preservatives such as the methyl, ethyl, propyl and butyl esters of hydroxybenzoic acid (Parabens-Mallinckrodt Chemical Corporation) EDTA and imidazolidinyl urea (Germall 115-Sutton Laboratories) at a level of from about 0.2% to about 2.5%; and
(e) An alkaline agent such as sodium hydroxide to neutralize, if desired, part of the fatty acids or thickener which may be present.

All of the percentages of these additional water phase components are of the total composition.

The present compositions may also contain agents suitable for aesthetic purposes such as dyes. The compositions of the present invention are preferably substantially free of materials that adversely affect their performance. Therefore, such things as polyethylene glycols are preferably present only at levels below about 1% of the total composition. The pH of the present compositions is preferably in the range of about 7.5–10.

Method of Manufacture

The compositions which comprise the skin lotion embodiments of the present invention generally have a lotion consistency and may be in the form of oil-in-water or water-in-oil emulsions with the former being preferred because of their more pleasing cosmetic properties. The compositions of the present invention are preferably made by the method comprising the steps of;
a) preparing the oil phase;
b) preparing the water phase; and
c) adding the oil phase to the water phase.

Step (a) is carried out by heating the oil phase materials to a temperature of about 75° C. to about 100° C. Step (b) is carried out by heating the water phase materials to a temperature about the same as that of the oil phase. The emulsion is formed by slowly adding the oil phase prepared in step (a) to the water phase prepared in step (b) with stirring. The pro-accords which comprise the fragrance delivery system or other ingredients may be added to the phase in which they are soluble prior to the mixing of the two phases or added directly to the mixed water and oil phases.

In addition to the fragrance-containing compositions for use on human skin, the pro-accords of the present invention are also suitable for use in any odor controlling or fragrance mediating application. An example of this odor control capacity is animal litter and odor control articles useful in lining the cages, stalls, and other living areas of domesticated animals. For example, U.S. Pat. No. 5,339,769 Toth et al., issued Aug. 23, 1994 describes a process for making an absorbent composition, which can well accommodate the pro-accord materials of the present invention.

An example of a suitable litter material which comprises the photo-labile pro-fragrance conjugates of the present invention can be formed by the following process.

A Glatt fluid bed granulator is charged with 1,0000 g of bentonite clay (90% of the particles being greater than 420 microns) and 10 g of a cellulose ether (Methocel ™ K15M Premium, a cellulose ether having a viscosity of 15,000 centipoise (cps) as a 2% aqueous solution). The granulator is started and the product temperature is brought up to about 40° C. (outlet temperature). When the outlet temperature reaches about 40° C., atomized water is sprayed onto the moving powders within the granulator, During the granulation process, inlet air temperature is maintained at 70° C. to 80° C.; air atomization pressure is 28–35 psi; and the spraying cycle is for 45 seconds with a 15 second shaking time.

The clay/cellulose ether agglomerates swell over time. The water hydrates the cellulose ether polymer, which produces adhesion to form the granule. At this time it is more advantageous to introduce the pro-accord materials and other aesthetic fragrances. The formation of the granule promotes aggregation of the small sized particles of the inert substrate, e.g. clay particles of about 50 to 600 microns. The formation of a granule significantly reduces the quality of dust in the final product while the litter forms an agglomerate when wetted.

In an alternative embodiment of the clay-based litter box articles/pro-accord admixture, once the clay particles have been formed, a concentrated solution, or a carrier alcohol-based admixture of the pro-accords may be delivered to the surface of the granule by a suitable means.

A deodorant gel stick of the present invention having the composition given below, and being essentially free of water, is prepared as follows.

TABLE I

| Ingredients | weight % | | | |
| --- | --- | --- | --- | --- |
|  | 5 | 6 | 7 | 8 |
| Dipropylene glycol | 39.85 | 51.95 | 75.10 | 71.15 |
| Sodium Stearate | 5.50 | 5.50 | 5.50 | 5.55 |
| PPG-3 myristyl ether | 29.40 | 25.33 | 15.00 | 19.30 |
| Cyclomethicone-D5 | 21.00 | 13.33 | — | — |
| Ethanol (absolute; 200 proof) | 1.80 | 1.44 | 1.95 | 1.50 |

TABLE I-continued

| Ingredients | weight % | | | |
|---|---|---|---|---|
| | 5 | 6 | 7 | 8 |
| Zinc pyrithione [1] | 0.05 | 0.05 | 0.05 | 0.10 |
| Conjugate [2] | 2.40 | 0.55 | 0.1 | 0.001 |

[1] Powder form commercially available from Olin.
[2] Photo-labile pro-fragrance conjugate according to Example 1.

All of the above materials, except the fragrance pro-accord, are vigorously mixed and heated to about 121° C. until the mixture is clear. The mixture is then cooled to about 80° C. and the pro-accord is added with stirring. The mixture is poured into stick molds and cooled to room temperature forming the deodorant gel stick compositions of the present invention.

A personnel cleanser composition is prepared by combining the following ingredients using conventional mixing techniques.

TABLE II

| Ingredients | weight % | | | |
|---|---|---|---|---|
| | 9 | 10 | 11 | 12 |
| Phase A | | | | |
| Water | QS 100 | QS 100 | QS 100 | QS 100 |
| Disodium EDTA | 0.100 | 0.100 | 0.100 | 0.100 |
| Glycerin | 4.00 | 4.00 | 4.00 | 4.00 |
| Methylparaben | 0.200 | 0.200 | 0.200 | 0.200 |
| $C_{10}$–$C_{30}$ alkyl acrylate crosspolymer [1] | 0.150 | 0.150 | 0.150 | 0.150 |
| Carbomer 954 [2] | 0.250 | 0.250 | 0.250 | 0.250 |
| Water | QS 100 | QS 100 | QS 100 | QS 100 |
| Phase B | | | | |
| Stearic Acid | 0.110 | 0.110 | 0.110 | 0.110 |
| Stearyl alcohol | 0.875 | 0.875 | 0.875 | 0.875 |
| Cetyl alcohol | 0.875 | 0.875 | 0.875 | 0.875 |
| Propylparaben | 0.150 | 0.150 | 0.150 | 0.150 |
| Steareth-2 | — | 0.25 | 0.25 | 0.25 |
| Steareth-21 | — | 0.50 | 0.50 | 0.50 |
| Phase C | | | | |
| Sodium hydroxide [3] | 0.130 | 0.130 | 0.130 | 0.130 |
| Phase D | | | | |
| Diisopropyl sebacate | 1.50 | 1.50 | 1.50 | 1.50 |
| Isohexadecane | 5.00 | 2.00 | 5.00 | 5.00 |
| Mineral Oil [4] | — | 5.00 | — | — |
| Phase E | | | | |
| Phenoxyethanol | 0.5 | 0.5 | — | 0.5 |
| Conjugate [5] | 1.5 | 1.5 | — | — |
| Conjugate [6] | — | — | 2.20 | 1.5 |
| Phase F | | | | |
| Glucose amide | 0.96 | 0.96 | 0.96 | 0.96 |
| Minors, aesthetics, carriers | balance | balance | balance | balance |

[1] Available as Pemulen ® from B. F. Goodrich Corporation.
[2] Available as Carbomer ® 954 from B. F. Goodrich Corporation.
[3] As a 50% aqueous solution.
[4] Light mineral oil available as Drakeol 5 from Penreco, Dickenson, TX.
[5] Photo-labile pro-fragrance conjugate according to Example 1.
[6] Photo-labile pro-fragrance conjugate according to Example 2.

The above Examples 8–11 can be suitably prepared as follows. In a suitable vessel, the Phase A ingredients are mixed at room temperature to form a dispersion and heated with stirring to 70–80° C. In a separate vessel, the Phase B ingredients are heated with stirring to 70–80° C. Phase B is then added to Phase A with mixing to form the emulsion. Next, Phase C is added to neutralize the composition. The Phase D ingredients are added with mixing, followed by cooling to 45–50° C. The Phase E ingredients are then added with stirring, followed by cooling to 40° C. Phase F is heated with mixing to 40° C. and added to the emulsion, which is cooled to room temperature. The resulting cleansing composition is useful for cleansing the skin. The emulsion de-emulsifies upon contact with the skin.

The present invention further relates to the use of photo-labile pro-fragrances in embodiments which do not contact human skin, inter alia, laundry detergent compositions, hard surface cleaning compositions, carpet cleaning compositions, and the like.

Surfactant System

The laundry detergent compositions of the present invention comprise a surfactant system. The surfactant systems of the present invention may comprise any type of detersive surfactant, non-limiting examples of which include one or more mid-chain branched alkyl sulfate surfactants, one or more mid-chain branched alkyl alkoxy sulfate surfactants, one or more mid-chain branched aryl sulfonate surfactants, one or more non mid-chain branched sulphonates, sulphates, cationic surfactants, zwitterionic surfactants, ampholytic surfactants, and mixtures thereof.

The total amount of surfactant present in the compositions of the present invention is from about 10% by weight, in one embodiment of the present invention the range of surfactant is from about 10% to about 80% by weight, of said composition. Another embodiment the amount of surfactant is from about 10% to about 60%, wherein another embodiment comprises from about 15% to about 30% by weight, of said composition.

Nonlimiting examples of surfactants useful herein include:

a) $C_{11}$–$C_{18}$ alkyl benzene sulfonates (LAS);
b) $C_6$–$C_{18}$ mid-chain branched aryl sulfonates (BLAS);
c) $C_{10}$–$C_{20}$ primary, α or ω-branched, and random alkyl sulfates (AS);
d) $C_{14}$–$C_{20}$ mid-chain branched alkyl sulfates (BAS);
e) $C_{10}$–$C_{18}$ secondary (2,3) alkyl sulfates as described in U.S. Pat. No. 3,234,258 Morris, issued Feb. 8, 1966; U.S. Pat. No. 5,075,041 Lutz, issued Dec. 24, 1991; U.S. Pat. No. 5,349,101 Lutz et al., issued Sep. 20, 1994; and U.S. Pat. No. 5,389,277 Prieto, issued Feb. 14, 1995 each incorporated herein by reference;
f) $C_{10}$–$C_{18}$ alkyl alkoxy sulfates ($AE_xS$) wherein preferably x is from 1–7;
g) $C_{14}$–$C_{20}$ mid-chain branched alkyl alkoxy sulfates ($BAE_xS$);
h) $C_{10}$–$C_{18}$ alkyl alkoxy carboxylates preferably comprising 1–5 ethoxy units;
i) $C_{12}$–$C_{18}$ alkyl ethoxylates, $C_6$–$C_{12}$ alkyl phenol alkoxylates wherein the alkoxylate units are a mixture of ethyleneoxy and propyleneoxy units, $C_{12}$–$C_{18}$ alcohol and $C_6$–$C_{12}$ alkyl phenol condensates with ethylene oxide/propylene oxide block polymers inter alia Pluronic® ex BASF which are disclosed in U.S. Pat. No. 3,929,678 Laughlin et al., issued Dec. 30, 1975, incorporated herein by reference;
j) $C_{14}$–$C_{22}$ mid-chain branched alkyl alkoxylates, $BAE_x$;
k) Alkylpolysaccharides as disclosed in U.S. Pat. No. 4,565,647 Llenado, issued Jan. 26, 1986, incorporated herein by reference;

l) Pseudoquat surfactants having the formula:

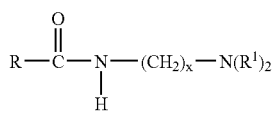

wherein R is $C_4$–$C_{10}$ alkyl, $R^1$ is selected from the group consisting of $C_1$–$C_4$ alkyl, —$(CH_2CHR^2O)_yH$, and mixtures thereof; $R^2$ is hydrogen, ethyl, methyl, and mixtures thereof; y is from 1 to 5; x is from 2 to 4; for the purposes of the present invention, a particularly useful pseudoquat surfactant comprises R equal to an admixture of $C_8$–$C_{10}$ alkyl, $R^1$ is equal to methyl; and x equal to 3; these surfactants are described in U.S. Pat. No. 5,916,862 Morelli et al., issued Jun. 29, 1999 included herein by reference;

m) Polyhydroxy fatty acid amides having the formula:

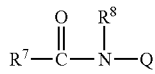

wherein $R^7$ is $C_5$–$C_{31}$ alkyl; $R^8$ is selected from the group consisting of hydrogen, $C_1$–$C_4$ alkyl, $C_1$–$C_4$ hydroxyalkyl, Q is a polyhydroxyalkyl moiety having a linear alkyl chain with at least 3 hydroxyls directly connected to the chain, or an alkoxylated derivative thereof; preferred alkoxy is ethoxy or propoxy, and mixtures thereof. These surfactants are described in U.S. Pat. No. 5,489,393 Connor et al., issued Feb. 6, 1996; and U.S. Pat. No. 5,45,982 Murch et al., issued Oct. 3, 1995, both incorporated herein by reference.

The mid-chain branched alkyl sulfate surfactants of the present invention have the formula:

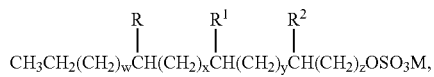

the alkyl alkoxy sulfates have the formula:

the alkyl alkoxylates have the formula:

wherein R, $R^1$, and $R^2$ are each independently hydrogen, $C_1$–$C_3$ alkyl, and mixtures thereof; provided at least one of R, $R^1$, and $R^2$ is not hydrogen; preferably R, $R^1$, and $R^2$ are methyl; preferably one of R, $R^1$, and $R^2$ is methyl and the other units are hydrogen. The total number of carbon atoms in the mid-chain branched alkyl sulfate and alkyl alkoxy sulfate surfactants is from 14 to 20; the index w is an integer from 0 to 13; x is an integer from 0 to 13; y is an integer from 0 to 13; z is an integer of at least 1; provided w+x+y+z is from 8 to 14 and the total number of carbon atoms in a surfactant is from 14 to 20; $R^3$ is $C_1$–$C_4$ linear or branched alkylene, preferably ethylene, 1,2-propylene, 1,3-propylene, 1,2-butylene, 1,4-butylene, and mixtures thereof.

M denotes a cation, preferably hydrogen, a water soluble cation, and mixtures thereof. Non-limiting examples of water soluble cations include sodium, potassium, lithium, ammonium, alkyl ammonium, and mixtures thereof.

Adjunct Ingredients

The following are non-limiting examples of adjunct ingredients useful in the laundry compositions of the present invention, said adjunct ingredients include builders, optical brighteners, soil release polymers, dye transfer agents, dispersents, enzymes, suds suppressers, dyes, perfumes, colorants, filler salts, hydrotropes, photoactivators, fluorescers, fabric conditioners, hydrolyzable surfactants, preservatives, anti-oxidants, chelants, stabilizers, anti-shrinkage agents, anti-wrinkle agents, germicides, fungicides, anti corrosion agents, and mixtures thereof.

The following are non-limiting examples of laundry detergent compositions according to the present invention.

TABLE III

| Ingredients | weight % | | | |
| --- | --- | --- | --- | --- |
| | 13 | 14 | 15 | 16 |
| Polyhydroxy coco-fatty acid amide | 2.50 | 4.00 | 4.50 | — |
| NEODOL 24-7 [1] | — | 4.50 | — | — |
| NEODOL 23-9 [2] | 0.63 | — | 4.50 | 2.00 |
| $C_{15}$ Alkyl ethoxylate sulphate | 20.15 | 4.00 | 5.50 | 20.50 |
| $C_{25}$ Alkyl sulfate | — | 14.00 | 15.00 | — |
| $C_{11.8}$ linear alkylbenzene sulfonate | — | — | — | 6.00 |
| $C_8$–$C_{10}$ Amidopropyl Amine | — | 1.30 | — | — |
| $C_{10}$ Amidopropyl Amine | 0.50 | — | — | 1.50 |
| Citric acid | 3.00 | 2.00 | 3.00 | 2.50 |
| $C_{12}$–$C_{18}$ fatty acid | 2.00 | 6.50 | 5.00 | 5.00 |
| Rapeseed fatty acid | — | 4.10 | — | 6.50 |
| Ethanol | 3.36 | 1.53 | 5.60 | 0.50 |
| Propanediol | 7.40 | 9.20 | 6.22 | 4.00 |
| Monoethanolamine | 1.00 | 7.90 | 8.68 | 0.50 |
| Sodium hydroxide | 2.75 | 1.30 | 0.75 | 4.40 |
| Sodium p-toluene sulfonate | 2.25 | — | 1.90 | — |
| Borax/Boric acid | 2.50 | 2.00 | 3.50 | 2.50 |
| Protease [3] | 0.88 | 0.74 | 1.50 | 0.88 |
| Lipolase [4] | — | 0.12 | 0.18 | — |
| Duramyl [5] | 0.15 | 0.11 | — | .0.15 |
| CAREZYME | 0.053 | 0.028 | 0.080 | 0.053 |
| Dispersant [6] | 0.60 | 0.70 | 1.50 | 0.60 |
| Ethoxylated polyalkyleneimine [7] | 1.20 | 0.70 | 1.50 | 1.20 |
| Optical Brightener | 0.13 | 0.15 | 0.30 | 0.15 |
| Conjugate [8] | 1.0 | 1.5 | 0.2 | 0.02 |

TABLE III-continued

| Ingredients | weight % | | | |
|---|---|---|---|---|
| | 13 | 14 | 15 | 16 |
| Pro-perfume [9] | 0.01 | — | 0.005 | — |
| Suds suppressor | 0.12 | 0.28 | 0.12 | 0.12 |
| Minors, aesthetics, stabilizers, water | balance | balance | balance | balance |

[1] $C_{12}$–$C_{14}$ alkyl ethoxylate as sold by Shell Oil Co.
[2] $C_{12}$–$C_{13}$ alkyl ethoxylate as sold by Shell Oil Co.
[3] Protease B variant of BPN' wherein Tyr 17 is replaced with Leu.
[4] Derived from Humicola lanuginqsa and commercially available from Novo.
[5] Disclosed in WO 9510603 A and available from Novo.
[6] Hydrophilic dispersant PEI 189 $E_{15}$–$E_{18}$ according to U.S. Pat. No. 4,597,898, Vander Meer, issued Jul. 1, 1986.
[7] Polyalkyleneimine dispersant PEI 600 $E_{20}$.
[8] Photo-labile pro-fragrance conjugate according to Example 3.
[9] Pro-perfume: 3-Amino-1-(2,6,6-trimethyl-cyclohex-3-enyl)-butan-1-one (10) according to Example 3.

As a non-limiting example, granular compositions are generally made by combining base granule ingredients, e.g., surfactants, builders, water, etc., as a slurry, and spray drying the resulting slurry to a low level of residual moisture (5–12%). The remaining dry ingredients, e.g., granules of the polyalkyleneimine dispersant, can be admixed in granular powder form with the spray dried granules in a rotary mixing drum. The liquid ingredients, e.g., solutions of the polyalkyleneimine dispersant, enzymes, binders and perfumes, can be sprayed onto the resulting granules to form the finished detergent composition. Granular compositions according to the present invention can also be in "compact form", i.e. they may have a relatively higher density than conventional granular detergents, i.e. from 550 to 950 g/l. In such case, the granular detergent compositions according to the present invention will contain a lower amount of "inorganic filler salt", compared to conventional granular detergents; typical filler salts are alkaline earth metal salts of sulphates and chlorides, typically sodium sulphate; "compact" detergents typically comprise not more than 10% filler salt.

Liquid detergent compositions can be prepared by admixing the essential and optional ingredients thereof in any desired order to provide compositions containing components in the requisite concentrations. Liquid compositions according to the present invention can also be in "compact form", in such case, the liquid detergent compositions according to the present invention will contain a lower amount of water, compared to conventional liquid detergents. Addition of the polyalkyleneimine dispersant to liquid detergent or other aqueous compositions of this invention may be accomplished by simply mixing into the liquid solutions the polyalkyleneimine dispersant.

The compositions of the present invention can be suitably prepared by any process chosen by the formulator, non-limiting examples of which are described in U.S. Pat. No. 5,691,297 Nassano et al., issued Nov. 11, 1997; U.S. Pat. No. 5,574,005 Welch et al., issued Nov. 12, 1996; U.S. Pat. No. 5,569,645 Dinniwell et al., issued Oct. 29, 1996; U.S. Pat. No. 5,565,422 Del Greco et al., issued Oct. 15, 1996; U.S. Pat. No. 5,516,448 Capeci et al., issued May 14, 1996; U.S. Pat. No. 5,489,392 Capeci et al., issued Feb. 6, 1996; U.S. Pat. No. 5,486,303 Capeci et al., issued Jan. 23, 1996 all of which are incorporated herein by reference.

The following are non-limiting examples of malodor abatement compositions utilizing the photo-labile conjugates of the present invention.

TABLE IV

| Ingredients | weight % | | | |
|---|---|---|---|---|
| | 17 | 18 | 19 | 20 |
| α-Cyclodextrin | 0.50 | — | 0.50 | — |
| Hydroxy α-cyclodextrin | — | 1.00 | — | — |
| Methylated β-cyclodextrin | — | — | 0.50 | — |
| Hydroxypropyl α-cyclodextrin | — | — | — | 0.27 |
| Hydroxypropyl β-cyclodextrin | 1.00 | 2.50 | — | 0.73 |
| γ-Cyclodextrin | 0.50 | 1.00 | — | — |
| Anti-microbial [1] | 0.001 | — | 0.0008 | 0.008 |
| Zinc chloride | — | — | 1.0 | 1.0 |
| Glutaraldehyde | — | 0.01 | — | — |
| Ethanol | — | 2.00 | — | — |
| Propylene glycol | — | — | — | 0.06 |
| Conjugate [2] | 1.5 | 0.2 | 0.01 | 0.002 |
| Distilled water | balance | balance | balance | balance |

[1] Kathon ® ICP/CG II (Rohm & Haas).
[2] According to Example 4.

The above compositions 16–19 can be prepared or used according to any of U.S. Pat. No. 5,534,165 Pilosof et al., issued Jul. 9, 1996; U.S. Pat. No. 5,593,670 Trinh et al., issued Jan. 14, 1997; U.S. Pat. No. 5,686,097 Trinh et al., issued Sep. 16, 1997; U.S. Pat. No. 5,714,137 Trinh et al. issued Feb. 3, 1998; U.S. Pat. No. 5,939,060 Trinh et al., issued Aug. 17, 1999; U.S. Pat. No. 6,146,621 Trinh et al., issued Nov. 14, 2000; all of which are included herein by reference.

The following is a fine fragrance accord suitable for use in a fine fragrance or perfume which comprises a photo-labile conjugate according to the present invention.

TABLE V

| Ingredients | Weight % | | | |
|---|---|---|---|---|
| | 21 | 22 | 23 | 24 |
| Pro-fragrance component | | | | |
| Pro-fragrance [1] | 1.0 | — | — | — |
| Pro-fragrance [2] | 2.0 | — | — | — |
| Pro-fragrance [3] | 2.0 | — | — | — |
| Pro-fragrance [4] | 2.0 | — | — | — |
| Pro-fragrance [5] | 0.9 | — | — | — |
| Free fragrance component | | | | |
| Damascone | 0.0001 | — | — | 0.001 |
| Melonal | 0.05 | — | — | 0.002 |
| Triplal | 0.01 | — | — | 0.002 |
| Undecavertol | — | — | — | 0.001 |
| Geraniol | — | — | — | 0.004 |
| Additional free fragrance raw materials [6] | 13.8 | 15.2 | 17.0 | 15.1 |
| Photo-labile pro-fragrance conjugate component | | | | |
| Conjugate [7] | 2.0 | 0.4 | 0.01 | 0.2 |
| Conjugate [8] | — | 0.4 | 0.02 | 0.08 |

TABLE V-continued

| | | | | |
|---|---|---|---|---|
| Conjugate [9] | — | 0.4 | 0.03 | 0.08 |
| Carrier [10] | balance | balance | balance | balance |

[1] Pro-fragrance according to U.S. Pat. No. 6,013,618 Morelli et al., issued Jan. 11, 2000, U.S. Pat. No. 6,077,821 Morelli et al., issued Jun. 20, 2000 or U.S. Pat. No. 6,087,322 Morelli et al., issued Jul. 11, 2000 which releases delta-damascone.

[2] Pro-fragrance according to U.S. Pat. No. 6,013,618 Morelli et al., issued Jan. 11, 2000, U.S. Pat. No. 6,077,821 Morelli et al., issued Jun. 20, 2000 or U.S. Pat. No. 6,087,322 Morelli et al., issued Jul. 11, 2000 which releases melonal.

[3] Pro-fragrance according to U.S. Pat. No. 6,013,618 Morelli et al., issued Jan. 11, 2000, U.S. Pat. No. 6,077,821 Morelli et al., issued Jun. 20, 2000 or U.S. Pat. No. 6,087,322 Morelli et al., issued Jul. 11, 2000 which releases triplal.

[4] Pro-fragrance according to U.S. Pat. No. 6,013,618 Morelli et al., issued Jan. 11, 2000, U.S. Pat. No. 6,077,821 Morelli et al., issued Jun. 20, 2000 or U.S. Pat. No. 6,087,322 Morelli et al., issued Jul. 11, 2000 which releases undecavertol.

[5] Pro-fragrance according to U.S. Pat. No. 6,013,618 Morelli et al., issued Jan. 11, 2000, U.S. Pat. No. 6,077,821 Morelli et al., issued Jun. 20, 2000 or U.S. Pat. No. 6,087,322 Morelli et al., issued Jul. 11, 2000 which releases geraniol.

[6] Conventional fragrance accord.

[7] Photo-labile pro-fragrance conjugate according to Example 3.

[8] Photo-labile pro-fragrance conjugate having the formula:

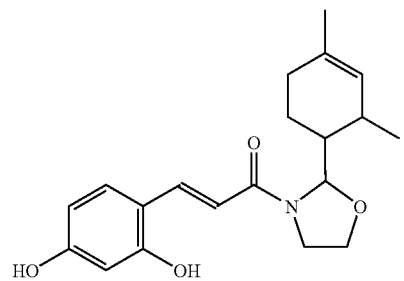

[9] Photo-labile pro-fragrance conjugate having the formula:

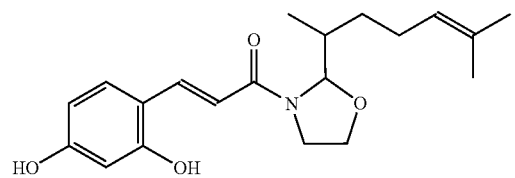

[10] Ethanol:water mixture (between 100:0 and 50:50).

The following are non-limiting examples of shampoo and hair conditioning compositions according to the present invention.

TABLE VI

| | weight % | | | |
|---|---|---|---|---|
| Ingredients | 25 | 26 | 27 | 28 |
| Ammonium Laureth-3 Sulfate | 14.00 | 14.00 | 14.00 | 14.00 |
| Cocamidopropyl betaine | 2.70 | 2.70 | 2.70 | 2.70 |
| Polyquaternium-10 | 0.15 | 0.15 | 0.15 | 0.30 |
| Light mineral oil | 0.30 | 0.15 | 0.05 | 0.30 |
| Cocamide MEA | 0.80 | 0.80 | 0.80 | 0.80 |
| Cetyl alcohol | 0.42 | 0.42 | 0.42 | 0.42 |
| Stearyl alcohol | 0.18 | 0.18 | 0.18 | 0.18 |
| Ethylene glycol distearate | 1.50 | 1.50 | 1.50 | 1.50 |
| Dimethicone | 1.00 | 1.00 | 1.00 | 3.00 |
| DMDM hydantoin | 0.37 | 0.37 | 0.37 | 0.37 |
| Additional free fragrances | 0.35 | 0.45 | 0.60 | 1.0 |

TABLE VI-continued

| | weight % | | | |
|---|---|---|---|---|
| Ingredients | 25 | 26 | 27 | 28 |
| Conjugate [1] | 0.001 | 0.05 | 0.5 | 1.50 |
| Distilled water | balance | balance | balance | balance |

[1] According to Example 3.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A photo-labile pro-fragrance conjugate having the formula:

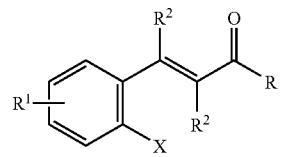

wherein R is an oxazolidine unit capable of releasing a fragrance raw material having the formula:

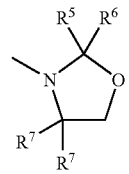

wherein $R^5$ units are selected from:
a) $C_6$–$C_{22}$ substituted or unsubstituted linear alkyl
b) $C_6$–$C_{22}$ substituted or unsubstituted branched alkyl;
c) $C_6$–$C_{22}$ substituted or unsubstituted linear alkenyl;
d) $C_6$–$C_{22}$ substituted or unsubstituted branched alkenyl;
e) $C_6$–$C_{22}$ substituted or unsubstituted cycloalkyl;
f) $C_6$–$C_{22}$ substituted or unsubstituted branched cycloalkyl;
g) $C_6$–$C_{22}$ substituted or unsubstituted cycloalkenyl;
h) $C_6$–$C_{22}$ substituted or unsubstituted branched cycloalkenyl;
i) $C_6$–$C_{22}$ substituted or unsubstituted aryl;
j) $C_6$–$C_{22}$ substituted or unsubstituted heterocyclicalkyl;
k) $C_6$–$C_{22}$ substituted or unsubstituted heterocyclicalkenyl;
l) and mixtures thereof;

$R^6$ is selected from the group consisting of hydrogen and methyl; each $R^7$ is independently hydrogen, methyl or —C(O)O$R^9$, and mixtures thereof;

$R^9$ is hydrogen, $C_1$–$C_{12}$ alkyl, and mixtures thereof;

each $R^1$ is independently hydrogen, a unit which can substitute for hydrogen selected from the group consisting of:
i) —NHCOR$^{30}$;
ii) —COR$^{30}$;
iii) —COOR$^{30}$;
iv) —COCH=CH$_2$;
v) —C(=NH)NH$_2$;
vi —N(R$^{30}$)$_2$;
vii) —NHC$_6$H$_5$;
viii) =CHC$_6$H$_5$;
ix) —CON(R$^{30}$)$_2$;
x) —CONHNH$_2$;
xi) —NHCN;
xii) —OCN;
xiii) —CN;
xiv) F, Cl, Br, I, and mixtures thereof;
xv) =O;
xvi) —OR$^{30}$;
xvii) —NHCHO;
xviii) —OH;
xix) —NHN(R$^{30}$)$_2$;
xx) =NR$^{30}$;
xxi) =NOR$^{30}$;
xxii) —NHOR$^{30}$;
xxiii) —CNO;
xxiv) —NCS;
xxv) =C(R$^{30}$)$_2$;
xxvi) —SO$_3$M;
xxvii) —OSO$_3$M;
xxviii) —SCN;
xxix) —P(O)H$_2$;
xxx) —PO$_2$;
xxxi) —P(O)(OH)$_2$;
xxxii) —SO$_2$NH$_2$;
xxxiii) —SO$_2$R$^{30}$;
xxxiv) —NO$_2$;
xxxv) —CF$_3$, —CCl$_3$, —CBr$_3$;
xxxvi) and mixtures thereof,
$C_1$–$C_{12}$ substituted or unsubstituted hydrocarbyl unit;
each $R^2$ is independently hydrogen, $C_1$–$C_{12}$ substituted or unsubstituted hydrocarbyl unit, and mixtures thereof;
X is —OH.

2. A compound according to claim 1 wherein R has the formula:

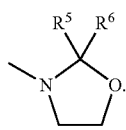

wherein $R^6$ is selected from the group consisting of hydrogen and methyl.

3. A conjugate according to claim 1 wherein R has the formula:

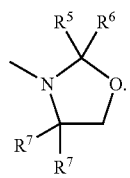

wherein $R^6$ selected from the group consisting of hydrogen and methyl; each $R^7$ is independently hydrogen, methyl or —C(O)OR$^9$, and mixtures thereof; $R^9$ is hydrogen, $C_1$–$C_{12}$ alkyl, and mixtures thereof.

4. A conjugate according to claim 1 having the formula:

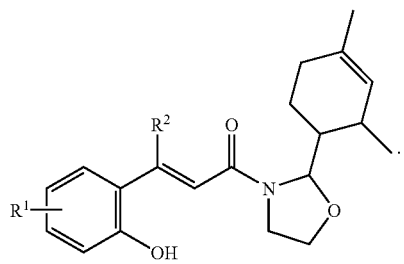

5. A conjugate according to claim 1 having the formula:

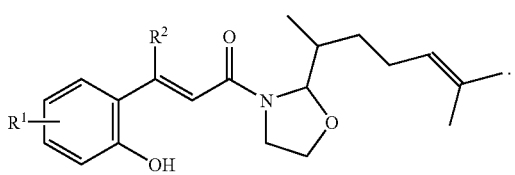

6. A photo-labile pro-fragrance conjugate delivery system comprising:
A) from about 0.001% by weight, of a photo-activated pro-fragrance conjugate according to claim 1; and
B) the balance carriers and adjunct ingredients.

7. A laundry detergent comprising:
A) from about 0.00 1% by weight, of a photo-activated pro-fragrance conjugate according to claim 1;
B) from about 10% by weight, of a detersive surfactant; and
C) the balance carriers and adjunct ingredients.

8. A perfume or fine fragrance comprising:
A) from about 0.001% by weight, of a photo-activated pro-fragrance conjugate according to claim 1;
B) from about 0.01% to about 99% by weight, of an admixture of fragrance raw materials; and
C) the balance carriers and adjunct ingredients.

9. A hair shampoo or conditioner comprising:
A) from about 0.001% by weight, of a photo-activated pro-fragrance conjugate according to claim 1;
B) from about 0.01% to about 5% by weight, of an admixture of fragrance raw materials; and
C) the balance carriers and adjunct ingredients.

* * * * *